United States Patent [19]

Roth et al.

[11] Patent Number: 5,779,673

[45] Date of Patent: Jul. 14, 1998

[54] DEVICES AND METHODS FOR APPLICATION OF INTRALUMINAL PHOTOPOLYMERIZED GELS

[75] Inventors: Laurence A. Roth, Windham, N.H.; Stephen J. Herman, Andover, Mass.; Farhad Khosravi, San Mateo, Calif.; David Melanson, Hudson; Michael Dumont, Stratham, both of N.H.; Patrick K. Campbell, Georgetown; John C. Spiridigliozzi, Dedham, both of Mass.

[73] Assignee: Focal, Inc., Lexington, Mass.

[21] Appl. No.: 494,333

[22] Filed: Jun. 26, 1995

Related U.S. Application Data

[63] Continuation-in-part of Ser. No. 256,448, Jun. 24, 1994, Pat. No. 5,665,063.

[51] Int. Cl.$^6$ .................................................. A61M 25/00
[52] U.S. Cl. ........................... 604/101; 604/102; 604/22; 604/280; 606/194
[58] Field of Search ........................... 604/22, 96, 102, 604/265, 266, 280, 264; 606/191–194, 198; 128/657, 772

[56] References Cited

U.S. PATENT DOCUMENTS

| | | |
|---|---|---|
| 3,707,146 | 12/1972 | Cook et al. . |
| 3,987,000 | 10/1976 | Gleichenhagen et al. . |
| 4,023,559 | 5/1977 | Gaskell . |
| 4,080,969 | 3/1978 | Casey et al. . |
| 4,118,470 | 10/1978 | Casey et al. . |
| 4,190,720 | 2/1980 | Shalaby . |
| 4,233,493 | 11/1980 | Nath . |
| 4,248,214 | 2/1981 | Hannah et al. . |
| 4,336,809 | 6/1982 | Clark . |
| 4,385,344 | 5/1983 | Gonser . |
| 4,423,725 | 1/1984 | Baran et al. . |
| 4,443,430 | 4/1984 | Mattei et al. . |
| 4,445,892 | 5/1984 | Hussein et al. . |
| 4,451,568 | 5/1984 | Schneider et al. . |
| 4,496,345 | 1/1985 | Hasson . |
| 4,573,966 | 3/1986 | Weikl et al. . |
| 4,575,181 | 3/1986 | Ishikawa . |
| 4,578,061 | 3/1986 | Lemelson . |
| 4,588,395 | 5/1986 | Lemelson . |
| 4,669,465 | 6/1987 | Moore et al. . |
| 4,744,366 | 5/1988 | Jang . |
| 4,763,653 | 8/1988 | Rockey . |
| 4,799,479 | 1/1989 | Spears . |
| 4,824,436 | 4/1989 | Wolinsky . |
| 4,832,688 | 5/1989 | Sagae et al. . |
| 4,846,165 | 7/1989 | Hare et al. . |
| 4,846,174 | 7/1989 | Willard et al. . |

(List continued on next page.)

FOREIGN PATENT DOCUMENTS

| | | |
|---|---|---|
| 0355200 | 2/1990 | European Pat. Off. . |
| 0402467 | 12/1990 | European Pat. Off. . |
| WO 88/03389 | 5/1988 | WIPO . |
| WO 89/12478 | 12/1989 | WIPO . |
| WO 90/01969 | 3/1990 | WIPO . |
| WO 91/12846 | 9/1991 | WIPO . |
| WO 91/17731 | 11/1991 | WIPO . |
| WO 92/21354 | 10/1992 | WIPO . |
| WO 93/16687 | 9/1993 | WIPO . |
| WO 93/17669 | 9/1993 | WIPO . |
| WO 94/05342 | 3/1994 | WIPO . |
| WO 95/08289 | 3/1995 | WIPO . |
| WO 95/09024 | 4/1995 | WIPO . |
| WO 96/00102 | 4/1996 | WIPO . |

*Primary Examiner*—Michael Powell Buiz
*Assistant Examiner*—Chalin Smith
*Attorney, Agent, or Firm*—Wolf, Greenfield & Sacks, P.C.

[57] ABSTRACT

Devices for providing polymeric layers on the interior surface of body lumens and spaces are disclosed. The devices can include proximal and distal occlusion elements to define the treatment space and an optical emitter to provide light for a photopolymerization procedure. The devices may include a molding member for providing a thick polymeric gel. Alternatively, devices without a molding member may be used to carry out an interfacial polymerization procedure.

72 Claims, 14 Drawing Sheets

U.S. PATENT DOCUMENTS

| | | | |
|---|---|---|---|
| 4,878,492 | 11/1989 | Sinofsky et al. . | |
| 4,900,303 | 2/1990 | Lemelson . | |
| 4,911,163 | 3/1990 | Fina . | |
| 4,938,763 | 7/1990 | Dunn et al. . | |
| 4,969,912 | 11/1990 | Kelman et al . | |
| 4,994,033 | 2/1991 | Shockey et al. | 604/101 |
| 5,059,178 | 10/1991 | Ya | 604/101 |
| 5,080,893 | 1/1992 | Goldberg et al. . | |
| 5,092,841 | 3/1992 | Spears . | |
| 5,100,429 | 3/1992 | Sinofsky et al. . | |
| 5,146,916 | 9/1992 | Catalini | 128/207.14 |
| 5,147,203 | 9/1992 | Seidenberg . | |
| 5,156,613 | 10/1992 | Sawyer . | |
| 5,169,395 | 12/1992 | Narciso, Jr. . | |
| 5,176,638 | 1/1993 | Don Michael . | |
| 5,196,005 | 3/1993 | Doiron et al. . | |
| 5,199,951 | 4/1993 | Spears . | |
| 5,207,670 | 5/1993 | Sinofsky . | |
| 5,209,748 | 5/1993 | Daikzono . | |
| 5,213,580 | 5/1993 | Slepian . | |
| 5,232,444 | 8/1993 | Just et al. . | |
| 5,250,070 | 10/1993 | Parodi . | |
| 5,256,141 | 10/1993 | Gencheff et al. | 604/53 |
| 5,257,970 | 11/1993 | Dougherty . | |
| 5,279,546 | 1/1994 | Mische et al. . | |
| 5,292,362 | 3/1994 | Bass et al. . | |
| 5,298,018 | 3/1994 | Narciso, Jr. . | |
| 5,306,249 | 4/1994 | Don Michel . | |
| 5,312,333 | 5/1994 | Churinetz et al. . | |
| 5,320,604 | 6/1994 | Walker et al. | 604/96 |
| 5,324,519 | 6/1994 | Dunn et al. . | |
| 5,328,471 | 7/1994 | Slepian . | |
| 5,336,178 | 8/1994 | Kaplan et al. | 604/53 |
| 5,364,356 | 11/1994 | Hofling | 604/96 |
| 5,372,585 | 12/1994 | Tiefenbrun et al. . | |
| 5,389,074 | 2/1995 | Parker et al. | 604/96 |
| 5,397,307 | 3/1995 | Goodin | 604/96 |
| 5,410,016 | 4/1995 | Hubbell et al. . | |
| 5,425,723 | 6/1995 | Wang . | |
| 5,454,794 | 10/1995 | Narciso et al. . | |
| 5,460,610 | 10/1995 | Don Michael . | |
| 5,462,529 | 10/1995 | Simpson et al. . | |
| 5,484,412 | 1/1996 | Pierpont | 604/101 |
| 5,523,092 | 6/1996 | Hanson et al. | 424/423 |
| 5,536,250 | 7/1996 | Klein et al. | 604/96 |
| 5,554,114 | 9/1996 | Wallace et al. | 604/53 |
| 5,665,063 | 9/1997 | Roth et al. . | |

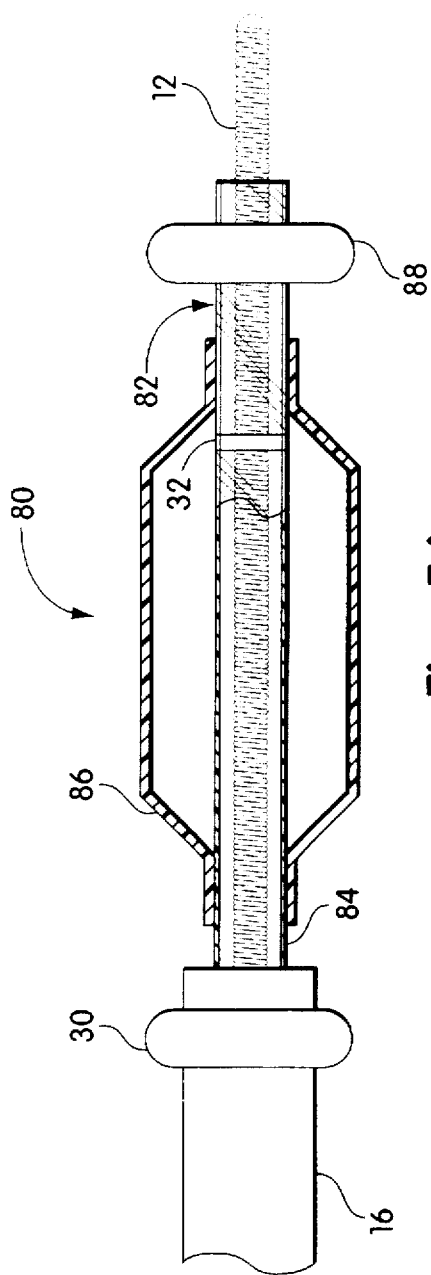
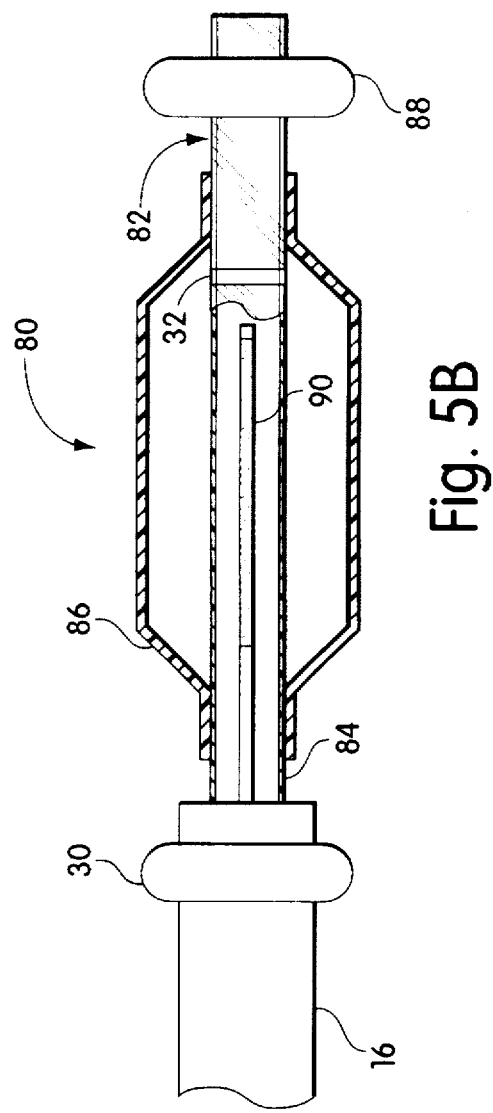
Fig. 5A
Fig. 5B

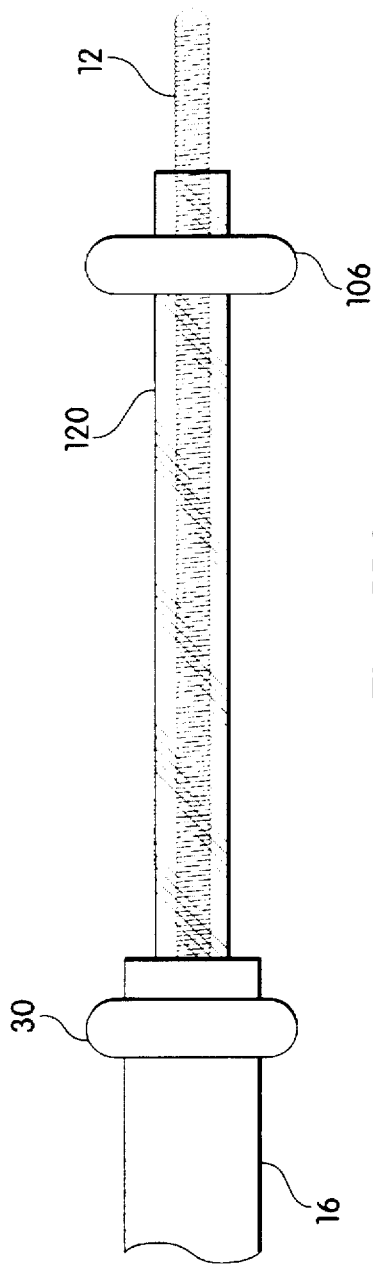
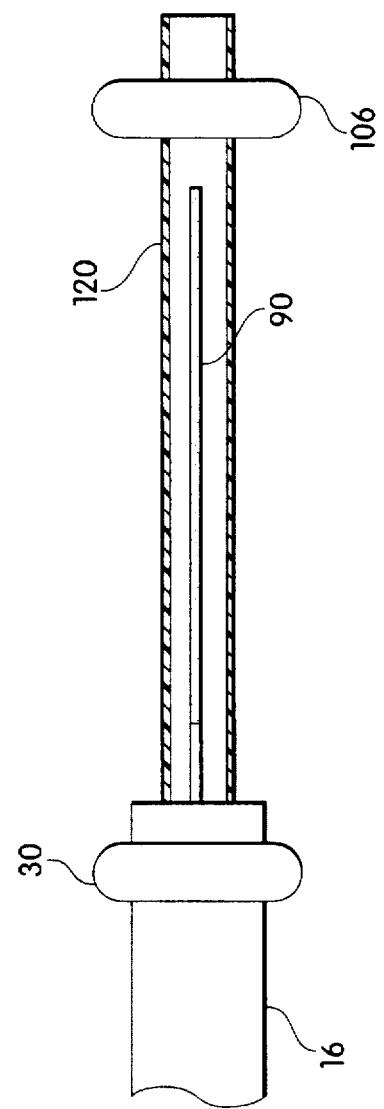
Fig. 11A
Fig. 11B

DEVICES AND METHODS FOR APPLICATION OF INTRALUMINAL PHOTOPOLYMERIZED GELS

RELATED APPLICATIONS

This application is a continuation-in-part of U.S. patent application Ser. No. 08/265,448, filed Jun. 24, 1994, now U.S. Pat. No. 5,665,063.

FIELD OF THE INVENTION

This invention relates to devices and methods for applying photopolymerizable gels to tissue lumens.

BACKGROUND OF THE INVENTION

U.S. Pat. No. 5,213,580, issued May 25, 1993 to Slepian et al., and International Patent Application Number PCT/US89/03593 by Slepian et al., published Mar. 8, 1990 as Publication Number WO 90/01969, both describe a system of endoluminal sealing in which a biodegradable polymer is introduced into the lumen of a blood vessel, positioned at a point of stenosis, and thermally reconfigured to seal and pave the interior of the vessel. International Patent Application Number PCT/US91/01242 by Slepian, published Sep. 5, 1991 as Publication Number WO 91/12846, describes a method for treatment of tubular organs in which a therapeutic agent is introduced into a region of a tissue lumen defined by two expansile members and allowed there to remain for a therapeutically effective period of time.

U.S. patent application Ser. No. 08/022,687, filed Mar. 1, 1993 and corresponding international publication no. WO93/17669 published Sep. 16, 1993 (Hubbell et al.), and U.S. patent application Ser. No. 08/024,657 filed Mar. 1, 1993 and corresponding international publication no. WO93/16687 published Sep. 2, 1993 (Hubbell et al.) disclose a number of photopolymerizable polymers that may be applied to living mammalian tissue, including living soft tissue in order to treat various medical conditions. For example, the polymers may be applied for the prevention of post-operative adhesions, protection of tissue surfaces, the local application of biologically active species, and the controlled release of biologically active agents to achieve local and systemic effects. The materials and conditions of application are selected to enhance desirable properties such as good tissue adherence without adverse tissue reaction, non-toxicity, good biocompatibility, biodegradability, and ease of application or handling.

The compositions that form the polymers generally include a light sensitive polymerization initiator applied as a coating to the tissue surface in a fluent form, such as a liquid. The coated tissue then is exposed to light to polymerize the composition in situ.

Reference is made to the above-identified patent applications for a detailed description of the various polymers, their compositions, manufacture and general use. The disclosures of the above-identified Hubbell et al. application Ser. Nos. 08/022,687 and 08/024,657 and international publication Nos. WO93/17669 and WO93/16687 are incorporated by reference, in their entireties, as part of the disclosure herein.

It is among the general objects of the present invention to provide devices and techniques for effectively and efficiently delivering and applying the liquid compositions (referred to as "prepolymers") to targeted tissue lumens, and then initiating the polymerization reaction in situ.

SUMMARY OF THE INVENTION

The invention includes devices for applying a polymeric material to a surface of a targeted tissue lumen, space, or cavity whether natural or induced, within a human or animal patient. The coating is applied as a prepolymer composition which then is exposed to electromagnetic radiation, such as irradiation with light, for example actinic light, to initiate and cause polymerization. In one embodiment, adapted for providing a "thick" gel to the interior surface of a lumen, the device comprises a catheter system including an elongated shaft having a distal end insertable into the lumen or cavity and a proximal end adapted to remain outside of the lumen or cavity. An emitter of electromagnetic radiation is supported by the shaft and a reservoir of prepolymer fluid is in fluid communication with the distal end of the shaft. According to one aspect, the device includes proximal and distal occlusion elements, such as radially expandable balloons, to define a treatment space, a molding member positioned between the occlusion elements to mold the prepolymer, and an optical emitter to provide a substantially uniform light field within the treatment space to uniformly polymerize the prepolymer.

In another embodiment, useful for providing a "thin" gel to the surface of a tissue lumen, the device comprises a catheter system as described above, optimally including proximal and distal occlusion elements to define a treatment space, and an emitter of electromagnetic radiation to provide a substantially uniform light field within the treatment space. Unlike the device used for providing a thick gel, in the thin-gel embodiment, a molding member positioned between the occlusion elements is not used.

In still another embodiment, either of the devices described above can have a single occlusion element. In this embodiment, rather than defining the treatment space as that area between proximal and distal occlusion elements, the treatment site is defined as that region extending a short distance from the occlusion element in which electromagnetic radiation from the emitter, the prepolymer, and an optional photoinitiator, converge. Additionally, for certain applications, the occlusion elements can be eliminated entirely.

According to another embodiment of the invention, a device for providing a polymeric coating on a surface of a body lumen or cavity is provided that includes an elongated shaft having a proximal end and a distal end adapted for insertion into a body lumen or cavity, an occlusion element supported by the shaft, and an injection lumen associated with the shaft that communicates with an injection port on the shaft for injection of a prepolymer fluid into a treatment space defined at least at one end by the occlusion element. The device also includes a reservoir of prepolymer fluid in fluid communication with the injection lumen, and an emitter of electromagnetic radiation positionable in the vicinity of the injection port.

In accordance with the above and other embodiments of the invention, the reservoir may include also an initiator of a polymerization reaction, in particular a photoinitiator. The photoinitiator may be admixed with the prepolymer fluid in the reservoir, or the photoinitiator and prepolymer fluid may be applied separately from the reservoir to a surface to be treated, via the catheter device. Alternatively, the device may include separate reservoirs, one for containing a prepolymer fluid and another for containing a polymerization initiator such as a photoinitiator.

According to certain embodiments of the invention, a solution containing at least one pharmaceutical agent is provided in fluid communication with the distal end of the shaft, and can be contained in one of the above-described reservoirs, or a separate additional reservoir. According to one aspect, the pharmaceutical agent is dissolved in the prepolymer fluid.

The invention also provides a device for insertion into a body lumen or cavity including an elongated shaft having a distal end insertable into the lumen or cavity and a proximal end adapted to remain outside of the lumen or cavity, and a proximal occlusion element and distal occlusion element each supported by the shaft, the proximal and distal occlusion elements defining therebetween a treatment space. At least one of the occlusion elements is a valve-occlusion balloon, and the proximal and distal occlusion elements are preferably each mounted near the distal end of the shaft. The valve-occlusion balloon can be relatively more compliant than the other occlusion element, can be inflated to a relatively lower pressure than the other occlusion element, can have a relatively thinner wall thickness, or be shaped so as to have a relatively lower area of contact with a wall of the lumen or cavity than the other occlusion element. The valve-occlusion balloon may be provided in conjunction with any others of the devices of the invention.

The invention also provides a flow-directing baffle mounted adjacent to an injection port in any of the devices of the invention. The baffle preferably is mounted so as to direct fluid from the injection port toward an occlusion element so as to flush a region at an interface of the occlusion element and the surface of the body lumen or cavity.

The invention also provides a flushing sleeve that can be utilized in conjunction with others of the devices of the invention. The flushing sleeve includes a tube with a plurality of radially-directed distribution ports in its surface, closely apposed to a shaft of the device, and joined to the shaft so as to create at least one axially-directed flushing port.

The invention also provides methods for applying a fluid to the interior surface of a body lumen or cavity. The fluid may contain a pharmaceutical agent, a polymerization initiator, a prepolymer species, a flushing fluid such as saline, other physiologically-acceptable fluids, or any combination of these. One method involves entering the lumen or cavity with a catheter having an elongated shaft that includes a distal end insertable into the lumen or cavity and a proximal end adapted to remain outside of the lumen or cavity, occluding the lumen or cavity with an occlusion element, and directing fluid toward the occlusion element so as to flush a region at an interface of the occlusion element and the surface of the lumen or cavity. Another method involves applying a fluid to an interior surface of a body lumen or cavity, and includes directing fluid in a first direction towards the surface of the lumen or cavity and simultaneously directing fluid within the lumen or cavity in a second direction perpendicular to the first direction.

In accordance with another method of the invention, a polymeric coating is formed on an interior surface of a body lumen or cavity. The method involves applying, from a distal end of a catheter, a photoinitiator to an interior surface of the body lumen or cavity, applying a prepolymer fluid to the interior surface of the body lumen or cavity, and polymerizing the prepolymer fluid adjacent the surface to form thereon a polymer coating. The photoinitiator may be admixed with the prepolymer fluid and applied simultaneously to the tissue surface, or the photoinitiator may be first applied to the tissue surface, followed by application of the prepolymer solution and polymerization.

The methods of the invention may be carried out with aid of any of the devices described herein.

It is among the general objects of the invention to provide a device for efficiently and effectively applying polymerizable materials to tissue, including living tissue, and for initiating polymerization of the composition in situ.

A further object of the invention is to provide an apparatus for applying either a thin or thick film of a polymer on a targeted tissue lumen.

Another object of the invention is to provide devices of the type described that are suited particularly, although not exclusively, for use in percutaneous, transluminal surgical applications.

DESCRIPTION OF THE DRAWINGS

The foregoing and other objects and advantages of the invention will be appreciated more fully from the following further description thereof, with reference to the accompanying drawings wherein:

FIGS. 5A and 5B are schematic representations of still another embodiment of a device for providing a thick polymeric film on a luminal wall.

FIGS. 11A and 11B are schematic representations of a third embodiment of a device for providing a polymeric barrier layer on a luminal wall.

DESCRIPTION OF THE PREFERRED EMBODIMENTS

The following detailed description of the invention is made in the context of use as an adjunct to percutaneous transluminal surgical procedures. It should be understood, however, that the invention may be used in other surgical environments where it may be beneficial to apply and polymerize material directly on tissue.

The devices of the present invention are adapted to allow a physician to apply a polymeric paving material to the interior of body lumens or spaces, whether natural or induced. The devices may be configured in a manner that allows the physician to provide either a thick polymeric coating or a thin "interfacial" coating on the tissue surface. In the case of devices for providing a thick coating, the device can include at least one occlusion element to define at least one end of a treatment space, a molding member to mold and shape the coating material into a desired configuration, and an optical emitter for transmitting light to the coating material in order to initiate polymerization of the material. Likewise, in the case of devices for the application of thin "interfacial" polymers, the devices can include at least one occlusion element to define at least one end of the treatment space, and an optical emitter for transmitting light to the coating material. Although, as will be described below, numerous embodiments of molding members and occlusion elements are contemplated, for the sake of simplicity, each of the molding members and occlusion elements shown in the Figures comprise inflatable balloons unless otherwise noted.

Figure 1:
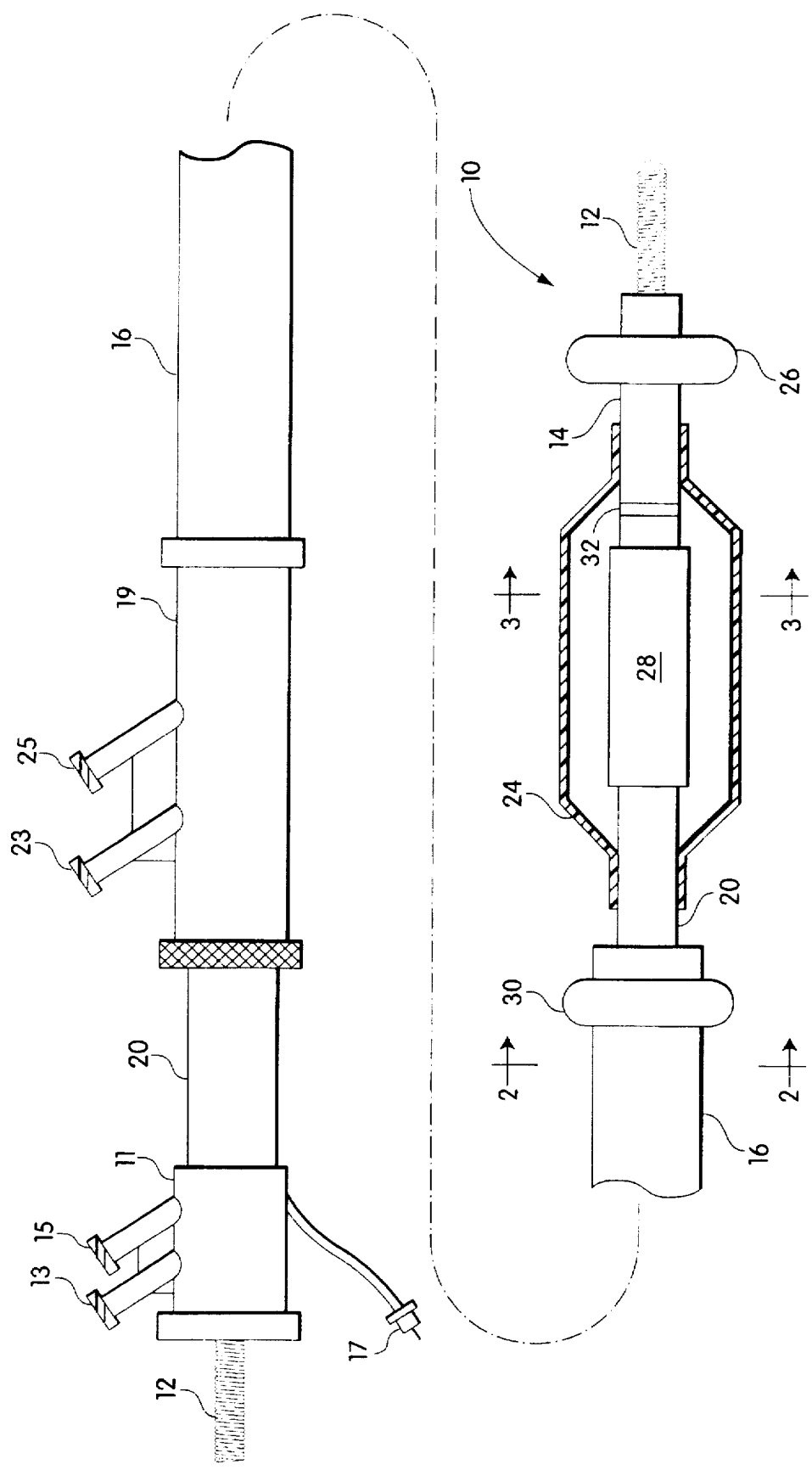
FIG. 1 is a schematic representation of one embodiment of a device for providing thick polymeric gels on the interior of a body lumen.

FIG. 1 is an illustration of one embodiment of a device for applying thick gels to tissue lumens. In the embodiment depicted in FIG. 1, the device 10 comprises three separate elements: a guidewire 12, a balloon catheter 14 and a sheath 16. The guidewire 12 may be any of a wide variety of guidewires known in the art for intraluminally guiding a catheter to a treatment site such as a coronary artery. The balloon catheter 14 comprises an elongated tubular shaft 20 having a central lumen, a molding member comprising molding balloon 24 and a distal occlusion element comprising distal occlusion balloon 26, both balloons being mounted near the distal end of the shaft 20. An optical emitter 28 is mounted within the interior of the molding balloon and serves to supply a substantially uniform field of light for carrying out the photopolymerization process in a manner described below. One or more radiopaque markers 32 comprising, for example, bands of a radiopaque metal such as tantalum, can optionally be positioned at various locations on the device. The sheath 16 includes two lumens. One is an annular space defined in part by the interior of the sheath, and is sufficiently large to surround the balloon catheter 14 when the molding balloon 24 and the distal occlusion balloon 26 are deflated. A second communicates with a proximal occlusion element which comprises a proximal occlusion balloon 30 mounted at or near the distal end of the sheath.

The proximal end of the device includes a hub assembly 11, having a central lumen to access the central lumen of the catheter shaft 20, a molding balloon inflation port 13, a distal occlusion balloon inflation port 15, and an optical fiber connector 17 which is attachable to a light source (not shown) to provide light to the optical emitter 28. An additional hub 19 is provided. Hub 19 is operatively connected to sheath 16 to serve as an actuator to position the sheath and the proximal occlusion balloon 30. Hub 19 also acts as a hemostatic valve. A collar 21 positioned at the proximal end of hub 19 allows the practitioner to position the sheath. Hub 19 includes a proximal occlusion balloon inflation port 23 and a treatment fluid injection port 25 through which fluids may be injected into the treatment space via an annular space (described below) between the interior of the sheath 16 and the exterior of the catheter shaft 20.

Figure 2:
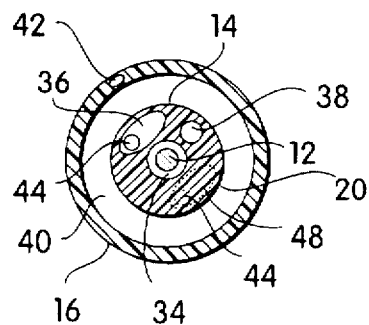
FIG. 2 is a cross-sectional view through line 2—2 of FIG. 1 at a region proximal to a proximal occlusion balloon.

As may be seen in FIG. 2, the shaft 20 of the balloon catheter 14 can include three lumens extending from its proximal end. A central lumen 34 provides a space through which the guidewire 12 may be passed. A molding balloon inflation lumen 36 communicates with the interior of the molding balloon 24 and molding balloon inflation port 13, thereby allowing the molding balloon to be inflated. Similarly, a distal occlusion balloon lumen 38 communicates with the interior of the distal occlusion balloon 26 and distal occlusion balloon inflation port 15, thereby allowing that balloon to be inflated.

In each embodiment described herein, the device need not be limited solely to catheters having a central lumen passing entirely though the catheter shaft. Rather, the catheters can include a separate, shorter lumen having one end which exits the catheter at or near the distal end of the catheter shaft and a second opening somewhat proximal to the distal end of the shaft. Such so-called "rapid exchange" or "monorail" catheters are designed to facilitate catheter exchanges while maintaining positioning of a guidewire. Monorail catheters are known in the art, being described, for example, in U.S. Pat. No. 4,762,129 to Bonzel.

As is also shown in FIG. 2, the sheath 16 surrounds the balloon catheter 14 and provides an annular space 40 through which fluids may be injected into a treatment space defined between the proximal 30 and distal 26 occlusion balloons. The sheath 16 includes a proximal occlusion balloon lumen 42 which communicates with the interior of the proximal occlusion balloon 30 and proximal occlusion balloon inflation port 23, and allows that balloon to be inflated.

Referring to FIG. 1, an optical emitter 28 is positioned within the interior of the molding balloon 24 and serves to direct light provided by at least one, and preferably a plurality of optical fibers 44 circumferentially outward in a substantially uniform manner. Referring again to FIG. 2, the optical fibers communicate with the emitter 28 either through the molding balloon inflation lumen 36, or, in the alternative, through a separate optical fiber lumen 48 (shown in phantom in FIG. 2) provided in the shaft 20.

Figure 3:
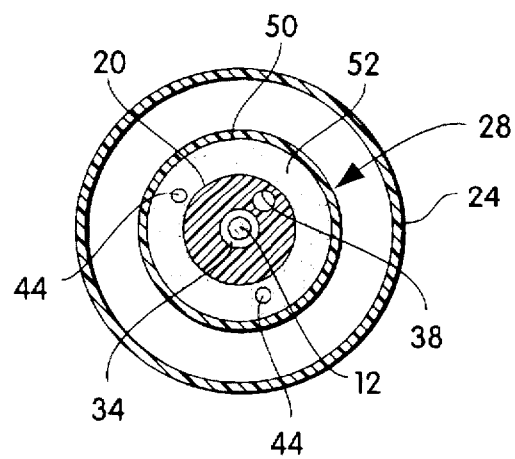
FIG. 3 is a cross-sectional view through line 3—3 of FIG. 1 at a region within a molding balloon.

In one embodiment, shown in FIG. 3, the optical emitter 28 comprises a flexible, translucent tube 50 containing a light scattering filler 52. The filler can comprise a translucent matrix containing a light-scattering medium such as titanium dioxide ($TiO_2$) particles. Other light scattering media suitable for use in accordance with the invention include $Zr_2O_3$, $Ba_2SO_4$, diamond dust, glass beads and combinations thereof, with or without $TiO_2$. The distal ends of the optical fibers 44 terminate within the light-scattering filler to allow light exiting from the fibers to be scattered in a substantially uniform radial and circumferential manner. In another embodiment, the catheter shaft 20 may be translucent at least at its distal end. A lumen passing through the translucent portion may be filled with a light-scattering filler as described above, and an optical fiber or fibers can be positioned within the filler. The optical fiber or fibers may be etched, cleaved, tapered or otherwise modified prior to insertion into the filler. The resulting catheter has, as an integral element, a light scattering optical emitter. The emitter may be attached to the optical fiber by taper joint, lap joint, or other known joining means.

A separate light source/controller (not shown) is connected to the proximal ends of the fibers via optical fiber connector 17 and serves to transmit light through the fibers into the emitter. By varying the concentration and composition of the scattering particles, and the number, positioning, and shape of the distal ends of the fibers, the intensity of the light field in the axial and circumferential directions can be controlled. Methods for achieving desired distributions of light intensity are known in the art and include simple arrays of scattering particles embedded in plastic as exemplified in U.S. Pat. No. 5,169,395 to Narciso, Jr.; and gradients of scattering particles as exemplified in U.S. Pat. No. 5,196,005 to Doiron et al.

The flexible, translucent tube 50 of the emitter 28 comprises a flexible material which minimizes absorption of light in a wavelength spectrum provided by the light source/controller. Numerous translucent polymeric materials including polyethylene terephthalate, polytetrafluoroethylene, polypropylene, silicone, and the like can be used. Polyethylene is preferred. The light scattering filler 52 preferably comprises a transparent or translucent matrix, for example an epoxy adhesive, containing the light-scattering particles. Like the emitter tube 50, the matrix containing the light-scattering particles must be substantially transparent to the wavelength spectrum of light which is to be passed through the emitter. Similarly, the molding balloon and the balloon inflation medium must be transparent to the light in order to allow the light to pass through the balloon and the medium and into the prepolymer material positioned in the treatment space between the proximal and distal occlusion balloons.

Figure 6:
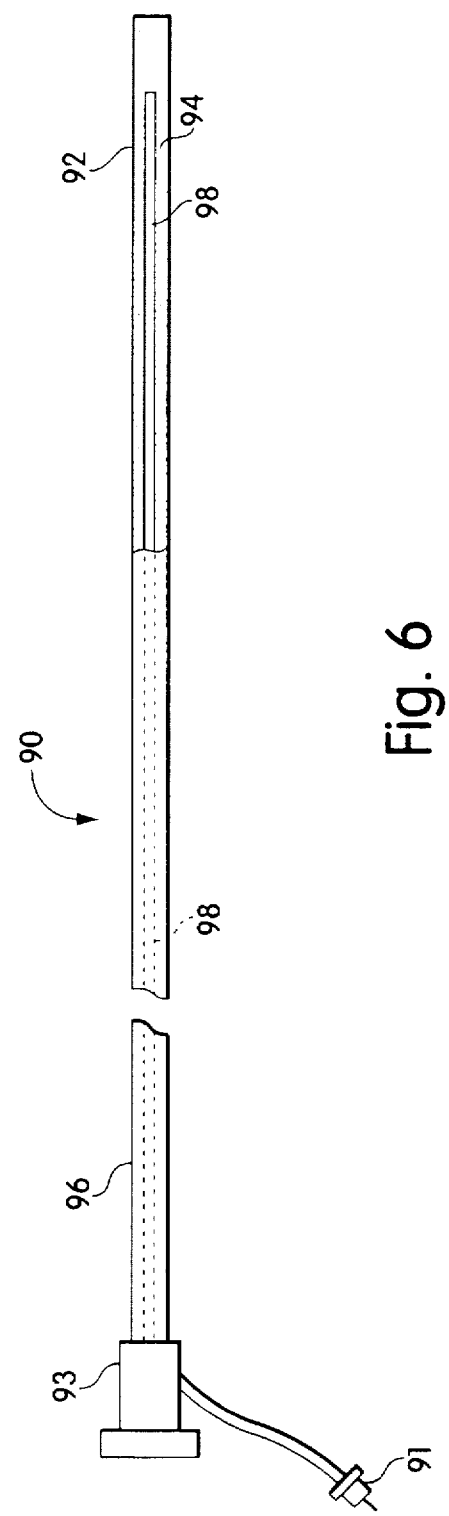
FIG. 6 is a schematic representation of an optical emitter catheter.

As an alternative, the emitter may be formed integrally on the distal end of the optical fibers themselves. For example, the distal end of the fibers may be chemically or mechanically modified in a manner which causes the fibers to radiate light laterally in the region of modification. Thus, in one embodiment, the distal end of the fibers may be ground or chemically modified to "frost" the fiber, thereby to provide light scattering sites directly on the fiber surface. Optical fibers modified in this manner can simplify the manufacture of the devices in that the need to assemble a separate optical emitter within the molding balloon portion of the device is eliminated. Still another emitter embodiment will be described below in connection with FIG. 6.

In one embodiment, the catheter shaft 20, at least in the region of the optical emitter 28, is transparent to light in the wavelength spectrum being used to prevent "shadowing" of the light. Alternatively, a reflective coating may be formed about the catheter shaft 20 in the region of the optical emitter to reflect any light scattered toward the shaft by the light scattering medium. For light in the visible spectrum, the reflective coating preferably comprises a thin coating of silver, and for light in the infrared spectrum, the reflective coating preferably comprises a thin coating of gold. Such coatings can be deposited using any of a variety of known methods for depositing metal on polymeric surfaces, including but not limited to sputtering, ion bombardment, and ion-assisted vapor deposition. It is noted that these modifications are not mandatory, however, as satisfactory results can still be achieved even if the shaft 20 in the region of the optical emitter 28 is not reflective of or translucent to the light. In that case, however, the catheter shaft must be such that it does not absorb light to the extent that it is heated to or above a temperature at which it will deform.

The catheter shaft 20 may be fabricated of any of a wide variety of materials that are sufficiently flexible and biocompatible. For example, polyethylenes, nylons, polyvinylchlorides, polyether block amides, polyurethanes, and other similar materials are all acceptable. It is preferred that the material have a low coefficient of friction, at least within the central lumen 34 to facilitate movement of the device over the guidewire 12. Alternatively, the central lumen 34 may be coated with a material to lower the frictional forces between the luminal walls and the guidewire. For example, if the catheter comprises a urethane, a polyethylene oxide-based material may be coated onto the lumens of the device to provide lubricity.

The molding balloon 24 comprises a non-compliant or is moderately compliant balloon such as those typically used in angioplasty procedures. Materials such as polyethylene terephthalates or crosslinked polyethylenes exhibit little change in maximum diameter over a wide range of inflation pressures, and accordingly offer desirable properties. Irradiated polyethylenes are also desirable in that they have low surface energy, thereby minimizing the effect of polymeric materials sticking to the molding balloon. Since non-compliant balloons, when inflated, maintain a substantially constant size regardless of their internal pressure, it is preferred that in the case of thick gel applications the balloon be sized approximately 0.20–1.0 mm less than the diameter of the vessel to be treated, thereby providing a gel coating on the interior of the lumen having a thickness of approximately 0.10–0.50 mm. In the alternative, a moderately compliant balloon such as one made of a urethane, a polyolefin or a nylon may be used. With moderately compliant balloons, a single device can be used to cover a wider range of treatment vessel diameters while allowing a tailored gel thickness.

At least part of the molding balloon, and the medium used to inflate the balloon, must be transparent to the light provided by the optical emitter. The balloon may be entirely transparent, or only the flatter portion parallel to the vessel wall may be transparent, with the conical portions coated to block the exciting light. A suitable inflation medium comprises a mixture of saline and an iodinated contrast agent. The mixture is both transparent to light provided by the emitter and radiopaque to allow fluoroscopic visualization when the balloon is inflated. It is preferred that the balloon be relatively thin walled so that its deflated condition will offer a low profile to facilitate delivery of the device through the sheath.

The balloon must readily release and not stick to the material which is to be photopolymerized. Polyethylene and polyolefin balloons have low energy surfaces and are therefore desirable. Alternatively, a coating having low surface energy may be used to facilitate release of the polymeric material from other balloons. Such coatings include silicone oils, fluoropolymers, surfactants, hydrogels or other materials having low surface energy.

Although shaped differently, the distal occlusion balloon may be formed of a material similar to that of the molding balloon. However, it is preferred that the distal occlusion balloon be formed of a relatively compliant material to offer the physician greater flexibility in the inflated size of the balloon in order to provide complete occlusion of the body lumen at the site at which the distal occlusion balloon is positioned. Furthermore, compliant occlusion balloons are likely to be less traumatic to the tissue lumen, thereby reducing the potential for complications as a result of over-inflation. Suitable compliant balloon materials include, but are not limited to latex, urethanes, polyether block amides, and the like. The distal occlusion balloon need not be transparent to light provided by the optical emitter.

The occlusion sheath 16 comprises an elongate flexible tube having a wall thickness on the order of about 0.003–0.004 inches, and an internal diameter large enough to contain the balloon catheter 14 when both the molding balloon 24 and the distal occlusion balloon 26 are in their deflated states. The interior diameter of sheath 16 must be substantially larger than the outer diameter of the balloon catheter shaft 20 in the region proximal to that region of shaft 20 extending distally from sheath 16 when shaft 20 is in its operative position. In this way, an annular space 40 is defined between the sheath and the shaft 20 through which the photopolymerizable prepolymer and other fluids may be injected into the treatment site, and through which other devices may be inserted if desired. Additionally, the sheath is axially moveable relative to the shaft in order to allow the shaft and its balloons to be withdrawn through the sheath to provide interchangability of such devices. Furthermore, by allowing relative axial movement between the proximal and distal occlusion balloons, the axial length of the treatment space may be varied, thereby allowing the physician to tailor the device to the particular lesion being treated.

It is desirable that the interior wall of the sheath lumen have a low coefficient of friction to facilitate movement of the sheath over the balloon catheter. Among the materials that may be used to form the sheath are fluoropolymers, high density polyethylenes, polyether block amides, thermoplastic elastomers, or urethanes. As described above, in cases in which the lumen does not offer a sufficiently low coefficient of friction, coatings such as surfactants, hydrogels, silicone oils or fluoropolymers may be provided. The sheath further includes a proximal occlusion balloon lumen 42 which communicates with the interior of the proximal occlusion balloon 30 to allow that balloon to be inflated. The proximal occlusion balloon 30 is of substantially the same construction as that of the distal occlusion balloon 26 described above.

The outer diameter of each of the device components should be sized appropriately to facilitate delivery and to minimize profile. As such, the device can be inserted within a targeted lumen causing minimal trauma at the treatment site. In one embodiment, for delivery within the coronary vessels, the profile of the occlusion sheath is preferably no larger than about 1.6 mm (about 0.065 inches) to allow delivery through a standard coronary guiding catheter. Likewise, the balloon catheter must be sized to move effectively within the sheath and to allow delivery of polymeric material in the space between the sheath inner diameter and the balloon catheter outer diameter. The device must also be sized to easily pass through obstructed lesions and to be deliverable over small diameter guidewires, such as guidewires having a diameter of approximately 0.30–0.45 mm (about 0.012–0.018 inches) commonly used in the coronary arteries.

In one method of use, the device is positioned at a treatment site, typically post-angioplasty, using standard percutaneous transluminal catheterization procedures. Prior to insertion of the device into a patient, each of the proximal occlusion balloon, distal occlusion balloon, and molding balloon are deflated and the distal end of the sheath is advanced to a location proximal to the distal end of the balloon catheter. In a post-angioplasty procedure, the guidewire used to position the dilatation catheter is left in place. If the procedure is carried out at a time other than post-angioplasty, the guidewire is inserted into a patient and navigated until its distal end crosses a treatment location. Subsequently, the device is passed over the guidewire until the molding balloon has been positioned at the desired treatment location. Since the distal occlusion balloon is, in this case, mounted on the same shaft as the molding balloon, positioning of the molding balloon serves to position the distal occlusion balloon as well. The proximal occlusion balloon is then positioned proximal to the molding balloon to define the proximal end of the area to be treated. Once inflated in the manner described below, the region between the proximal occlusion balloon and the distal occlusion balloon defines a space that is referred to herein as the "treatment space".

Once the molding balloon is positioned at a desired treatment position and the proximal and distal occlusion balloons are positioned with desired spacing, the occlusion balloons are inflated to define the treatment space and to occlude the body lumen at both the proximal and distal ends of the treatment space. It is preferred that the proximal occlusion balloon be inflated prior to the distal occlusion balloon to allow blood and other biological fluids contained within the body lumen to be removed prior to sealing the treatment space between both occlusion balloons.

If desired, following inflation of the proximal occlusion balloon, the treatment space may be filled or flushed with a solution, such as an inert saline solution, to remove blood and other biological fluids from the treatment space prior to inflation of the distal occlusion balloon. The solutions may be introduced through a port such as a side arm on a Touhey-Borst adapter or a similar device positioned at or near the proximal end of the catheter shaft. In addition, or as an alternative, a non-inert solution such as a solution containing a pharmaceutical agent may be injected into the treatment space. Among the non-inert solutions, solutions of tPA, streptokinase, urokinase, and the like are preferred, although virtually any pharmaceutical or therapeutic agent capable of being applied using the devices disclosed herein and offering a desired pharmaceutical or therapeutic effect may be used, either alone or in various combinations. Additionally, it is contemplated that one or more therapeutic agents for treatment of tissue or for preventing the deposition of substances from body fluid contained in the vessel may be incorporated into a prepolymer solution.

As used herein, pharmaceutical or therapeutic agent refers to substances which alter the metabolism of cells or which reduce the tendency for thrombosis or morbidity within diseased portions of the tissue. Examples for use in coronary artery applications are vasodilating agents i.e., nitrates and calcium channel blocking drugs; anti-proliferative agents i.e., colchicine and alkylating agents; intercalating agents; growth modulating factors such as interleukins, transformation growth factor b, congeners of platelet derived growth factor and monoclonal antibodies directed against growth factors; anti-thrombotic agents, e.g., anti-GIIb/IIIa, trigramin, prostacyclin, salicylates, and tissue-factor pathway inhibitors; thrombolytic agents e.g., streptokinase, urokinase, tissue plasminogen activator (tPA) and anisoylated plasminogen-streptokinase activator complex (APSAC); anti-inflammatory agents, both steroidal and nonsteroidal and other agents which may modulate vessel tone, function, arteriosclerosis, and the healing response to vessel or organ injury post intervention. Anti-proliferative drugs or high efficacy anti-inflammatory drugs are also useful for treatment of focal vasculitides or other inflammatory arteritidies, e.g., granulomatous arteritis, polyarteritis nodosa, temporal arteritis and Wegner's granulomatosis. Anti-inflammatory agents are also useful in connection with indications such as inflammatory bowel disease, Crohn's disease, ulcerative colitis and focal GI inflammatory diseases. In other applications, adhesives may be introduced in accordance with the invention to help heal dissections, flaps and aneurysms. Exemplary adhesives include cyanoacrylates, gelatin/resorcinal/formol, mussel adhesive protein and autologous fibrinogen adhesive. The term "therapeutic agents" does not encompass solubilizing or dissolving agents which disrupt the atherosclerotic plaque.

The flushing liquids may be injected into the treatment space through the annular space 40 between the sheath 16 and the balloon catheter shaft 20. Once the treatment space has been cleared of blood and other biological fluids, the distal occlusion balloon is inflated to thereby seal and define the treatment space.

As an alternative, the device may be provided with an additional flushing, or drain lumen whereby the flushing liquids injected into the treatment space exit through the additional lumen and out of the patient through the proximal end of that lumen. It is noted that since all liquids (i.e., flushing, prepolymer, photoinitiator) used in connection with the invention are biologically compatible, they need not be removed from the patient, but rather may be allowed to flow distally from the treatment site for later, natural biological, removal.

The device may also be provided with a perfusion lumen that allows blood to bypass the treatment space during the treatment process. In particular, such a lumen includes one or more ports which communicate with the exterior of the catheter at a location proximal to the proximal occlusion element and distal to the distal occlusion element. During occlusion at one or both ends of the treatment space, blood can enter the perfusion lumen through the proximal perfusion port, travel within the perfusion lumen through the treatment space, and return to the blood vessel through the distal perfusion port. Thus, even if the occlusion elements are expanded for an extended period of time, some blood flow across the treatment space is provided, thereby providing blood to the lumen distal to the treatment space.

Following the optional flushing step, a prepolymer fluid to be photopolymerized is injected into the treatment space through the annular space 40. If an additional flushing lumen or a valve-occlusion balloon (described below) is not provided, it is preferred that the distal occlusion balloon be deflated simultaneously with injecting the prepolymer fluid into the treatment space. In this manner, the flushing fluid that occupies the treatment space prior to prepolymer injection will be displaced distally by the prepolymer. Once the prepolymer has replaced the flushing fluid in the treatment space, the distal occlusion balloon is inflated to contain the prepolymer. Alternatively, if a "flushing" lumen is provided, the flushing fluid can be displaced by the prepolymer and removed through that lumen. Although the prepolymer is described in detail in the aforementioned Hubbell applications, it is noted that it preferably contains a photoinitiator to cause crosslinking in the prepolymer upon exposure to light.

Once the prepolymer fluid has entered the treatment space, the molding balloon is inflated to thereby form the prepolymer fluid into an annular "sleeve" in contact with the interior surface of the body lumen. As noted above, the molding balloon is preferably expanded to a size which provides a clearance of between approximately 0.10 and 0.50 mm between the balloon surface and the interior surface of the body lumen. It is noted, however, that much greater clearance may be provided if thicker gels are desired. For example, the present invention could be used to provide gels having a thickness of 10 mm or greater if desired for a particular application. Thus, one primary function of the molding balloon is to provide a means for maintaining a patent lumen of predefined diameter following gel formation within the body lumen. As the molding balloon is inflated, excess prepolymer fluid will be forced back into the annular space 40 and the optional flushing lumen. Some fluid may also be forced past the occlusion elements, however, since the fluid is biocompatible, the excess fluid does not present a problem. Inflation of the balloon to the desired size can be monitored using fluoroscopy.

Upon expansion of the molding balloon, light energy is supplied through the optical fibers to the optical emitter. The light diffuses outwardly from the emitter, and through the balloon inflation medium and the balloon. Upon transmission through the balloon, the light energy is absorbed by the photoinitiator contained in the prepolymer fluid thereby causing the prepolymer to become crosslinked. Upon completion of the crosslinking procedure, the light source is turned off and the molding balloon is deflated, thereby leaving a polymeric sleeve having a thickness of approximately 0.10–0.50 mm on the interior surface of the body lumen. The proximal and distal occlusion balloons are then deflated and the device is withdrawn from the body lumen, leaving the sleeve in place.

It is noted that the specific sequence of the balloon inflation and light irradiation steps is intended merely as an example, and that many variations to the sequence are contemplated as well. For example, the molding balloon may be inflated simultaneously with introduction of light to the prepolymer material, or the photopolymerization process may be initiated prior to inflation of the molding balloon.

Additionally, as noted above, the device can be constructed to have only a single, proximal or distal occlusion balloon. In that case, rather than defining the treatment space by the sequential or simultaneous inflation of; the proximal and distal occlusion balloons, the single occlusion balloon is inflated, the flushing liquid is injected, followed immediately by the injection of the prepolymer liquid. Upon injection of the prepolymer, photopolymerization is carried out as described above. In that case, the treatment space can be defined, in more general terms, as an area at which the polymer, light and tissue physically intersect at a given time.

Additionally, in some circumstances, it is possible to eliminate the occlusion balloons altogether. For example, if the polymeric material is to be applied to the surfaces of a natural or induced body lumen or space through which a body fluid is not continuously flowing, occlusion of the region to be treated can be eliminated if the body fluid can be adequately displaced by the injection of flushing solutions and/or the prepolymer liquid.

It is also noted that the elements of the device described above need not be separate. Rather, a single shaft incorporating any or all of the occlusion balloons, molding balloon, and optical emitter can be used to apply polymeric material to tissue surfaces using the methods described above.

Figure 4:
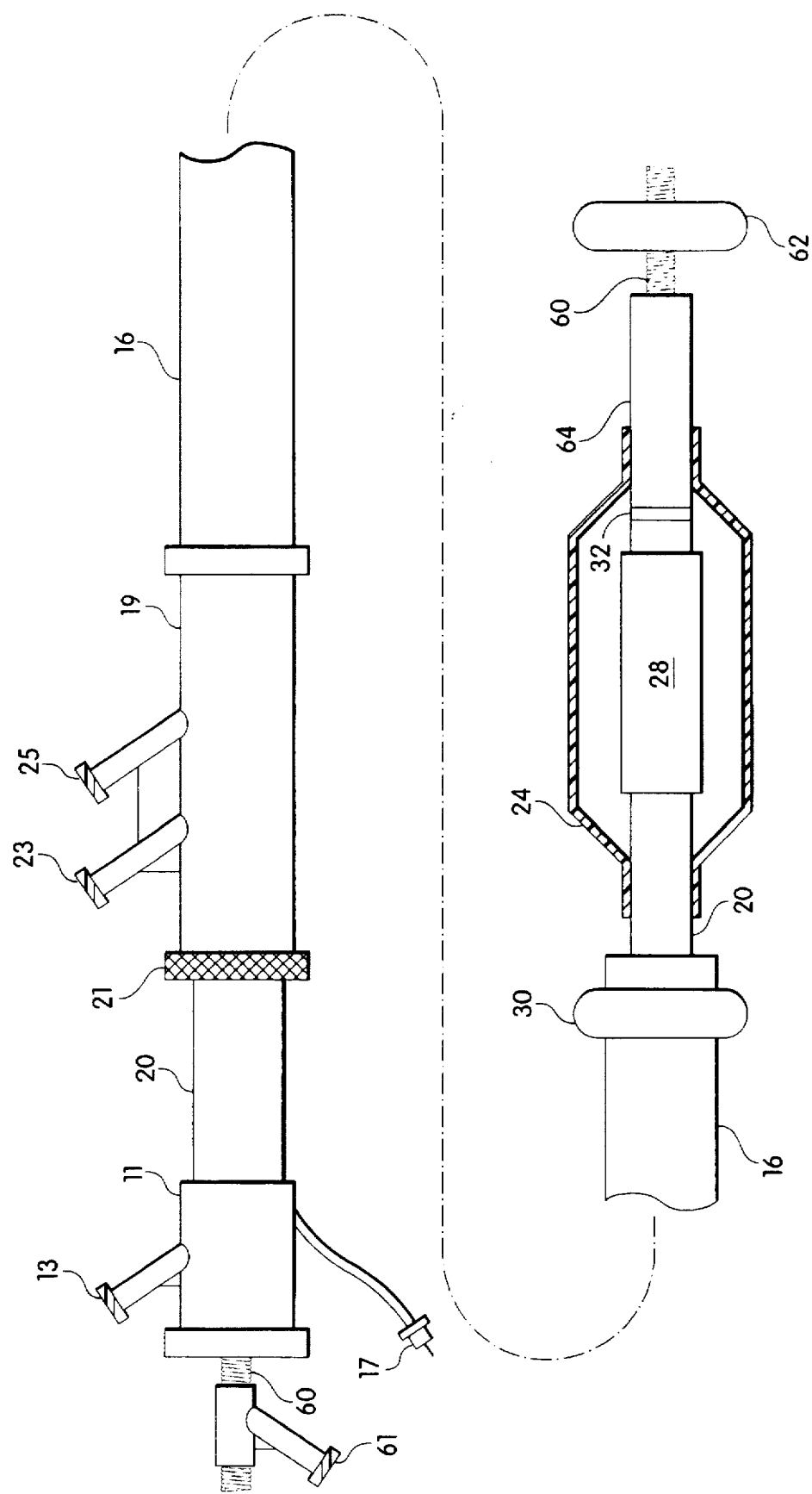
FIG. 4 is a schematic representation of a second embodiment of a device for providing thick polymeric gel on a luminal wall.

Another embodiment of the device is depicted schematically in FIG. 4. Although similar to the device of FIG. 1 in many aspects, the device of FIG. 4 differs in that the distal occlusion balloon is positioned on the guidewire, rather than on the balloon catheter shaft in the region distal to the molding balloon. Thus, the device comprises a guidewire 60 having a distal occlusion balloon 62 positioned at its distal end. Such so-called "balloon-on-a-wire" devices are known in the art, being described, for example in U.S. Pat. No. 4,582,181 to Samson and in U.S. Pat. No. 4,846,174 to Willard et al. The balloon catheter 64 is identical to that described previously with the exception that it does not include the distal occlusion balloon 62 or a lumen communicating with that balloon. In all other aspects, the molding balloon 24, the optical emitter 28, the sheath 16, the proximal occlusion balloon 30, and the marker 32 are identical to those described previously. Likewise, the proximal end of the device is similar to that of FIG. 1 with the exception that the distal occlusion balloon inflation port 61 has been positioned on the guidewire 60 consistent with the "balloon-on-a-wire" design.

Still another embodiment of the device is depicted schematically in FIGS. 5A and 5B. In that embodiment, the optical emitter is not included as part of the balloon catheter assembly, but rather, comprises a separate element that is inserted through the central lumen of the balloon catheter during the treatment procedure. More particularly, such a device 80 comprises three separate elements: a guidewire 12, a balloon catheter 82 and a sheath 16. As before, the guidewire 12 may be any of a variety of guidewires known in the art for intraluminally guiding a catheter to a treatment site. The balloon catheter 82 comprises an elongated tubular shaft 84 having a molding balloon 86 and a distal occlusion balloon 88, both mounted near the distal end of the shaft 84. One or more radiopaque markers 32 may be positioned on the balloon catheter shaft 84. The sheath 16 includes a lumen having a diameter sufficiently large to receive and enable passage of the balloon catheter 82 when the molding balloon 86 and the distal occlusion balloon 88 are deflated. A proximal occlusion balloon 30 is mounted at or near the distal end of the sheath.

The shaft 84 of the balloon catheter 82 includes at least three lumens: a first lumen communicating with the interior of the distal occlusion balloon 88, a second lumen communicating with the interior of the molding balloon 86 and a third lumen passing entirely through the shaft through which the guidewire. 12 may be passed. The proximal end of the device is similar to that of FIG. 1 with the exception of the optical fiber connector 17 which is absent in the embodiment of FIG. 5A.

The device 80 further includes a separate optical emitter 90 that may be inserted through the balloon catheter shaft 84 after the guidewire 12 is removed. In one embodiment, depicted in FIG. 6, the optical emitter 90 has, at its distal end, a flexible, translucent tube 92 containing a light scattering filler 94, such as that described previously. The filler 94 is contained at the distal end of an elongated emitter shaft 96 having a central lumen therethrough. At least one optical fiber 98 passes through the lumen of the emitter shaft 26 and has its distal end terminating within the light scattering filler 94. The proximal end of the optical fiber 98 is connected to the light source/controller (not shown) via an optical fiber connector 91 which accesses the emitter shaft 96 through a proximal hub 93. One or more radiopaque markers may be provided on the emitter to assist in determining the position of the emitter once it is inserted into the patient.

The emitter tube 92 must be formed of a material that is substantially translucent or transparent to the light delivered through the optical fiber. Numerous translucent polymeric materials can be used, however, polyethylene is preferred. As an alternative, rather than mounting the emitter tube 92 on the distal end of the emitter shaft 96, the emitter tube and emitter shaft may be a single integral shaft formed of a translucent or transparent material and loaded with the light scattering filler only at its distal end. In another embodiment, a single optical fiber having a emitter positioned at its distal end may be used. In this embodiment, as before, the emitter comprises a transparent or translucent tube filled with a transparent or translucent binder material and a light scattering medium. The distal end of the optical fiber is inserted a short distance into the proximal end of the emitter, thereby providing a source of light to the emitter. As yet another alternative, the fiber can be inserted into an emitter formed of a translucent polymer having either inherent scattering characteristics or scattering media compounded therein. As still another alternative, at least one optical fiber having its distal end chemically or mechanically modified to radiate light laterally can be substituted for or combined with the emitters described above.

As with the other embodiments, in use, the device is positioned at a treatment site, typically post-angioplasty, using percutaneous transluminal catheterization procedures. Prior to insertion into a patient, the balloons of the device are deflated and the distal end of the sheath is advanced over the balloon catheter to a location proximal to the distal end of the catheter. The device is passed over the previously placed angioplasty guidewire until the molding balloon is positioned at the treatment location. The proximal occlusion balloon is then positioned at a desired proximal position. Once the molding balloon is positioned at a desired treatment position and the proximal and distal occlusion balloons are positioned with desired spacing, the occlusion balloons are inflated and the guidewire is withdrawn. As before, the balloons may be inflated either simultaneously or sequentially, the order being determined, in part, by the need to displace fluid in the treatment space prior to introduction of the prepolymer material. A flushing step, as described above, may optionally be performed.

After the guidewire has been withdrawn, the optical emitter 90 is inserted through the central lumen of the balloon catheter shaft 84 and advanced to position the emitter tube 92 in the portion of the shaft 84 surrounded by the molding balloon 86. A prepolymer material containing a dye or other photoinitiator is injected into the treatment space between the proximal 30 and distal 88 occlusion balloons and then molded and photopolymerized by expansion of the molding balloon 86 and illuminated with light from the optical emitter 90 in the manner described previously. Unlike the earlier embodiment, however, the balloon catheter shaft 84, at least in the region of the optical emitter tube 92, must be substantially transparent or translucent to light radiating from the emitter in order to allow that light to pass into and through the molding balloon. Upon completion of the crosslinking procedure, the light source is turned off and the molding balloon, the proximal occlusion balloon and the distal occlusion balloon are each deflated and the device is withdrawn from the body lumen, leaving a photopolymerized sleeve of polymeric material in place within the body lumen.

Each of the aforementioned embodiments is directed to a device for providing a relatively thick (i.e., about 0.10–0.50 mm) polymeric coating on the interior of a body vessel. In another embodiment, however, the device may be used to conduct: an interfacial polymerization procedure to form a relatively thin (i.e., about 0.005–0.10 mm) barrier coating on the interior surface of a body lumen. Unlike the thick gel method described above in which the polymer contains a photoinitiator, the interfacial polymerization procedure involves, as a preliminary step, contacting the surface to be treated with a photoinitiator for a time sufficient to allow the tissue surface to adsorb a portion of the photoinitiator, and then contacting that surface with a polymer solution while simultaneously or subsequently irradiating the interface with light. The light interacts with the photoinitiator at the tissue surface causing a polymer film to crosslink and "grow" from the tissue surface into the lumen. After a brief period, the unpolymerized solution is removed from the treatment space leaving behind a thin barrier layer of crosslinked polymer on the luminal surface. Each of the thick gel and thin barrier layer processes are described in detail in the aforementioned, previously incorporated, Hubbell application Ser. Nos. 08/024,657 and 08/022,687 and corresponding international publication Nos. WO93/16687 and WO93/17669. For example, prepolymer solutions can include macromers made up of a biodegradable region, preferrably hydrolyzable under in vivo conditions, a water soluble region, and at least two polymerizable regions. The polymerizable regions have the capacity to form covalent bonds resulting in macromer interlinking, for example, carbon-carbon double bonds of acrylate-type molecules. Such polymerization is characteristically initiated by free-radical formation resulting, for example, from photon absorbtion of certain dyes and chemical compounds to ultimately produce free radicals. The polymerizable species generally contains ethylenically unsaturated groups, for example acrylates, diacrylates, oligoacrylates, methacrylates, dimethacrylates, oligomethacrylates, or other biologically acceptable photopolymerizable groups. Useful photoinitiators are those which can be used to initiate by free radical generation polymerization of the macromers without cytotoxicity and within a short time frame. Prefererd dyes as initiators for UV or visible light initiation are ethyl eosin, 2, 2-dimethoxy-2-phenyl acetophenone, other acetophone derivatives, and camphorquinone. These and other polymerizable species and photoinitiators are described in the above-reference Hubbell U.S. patent applications and international publications.

Figure 7:
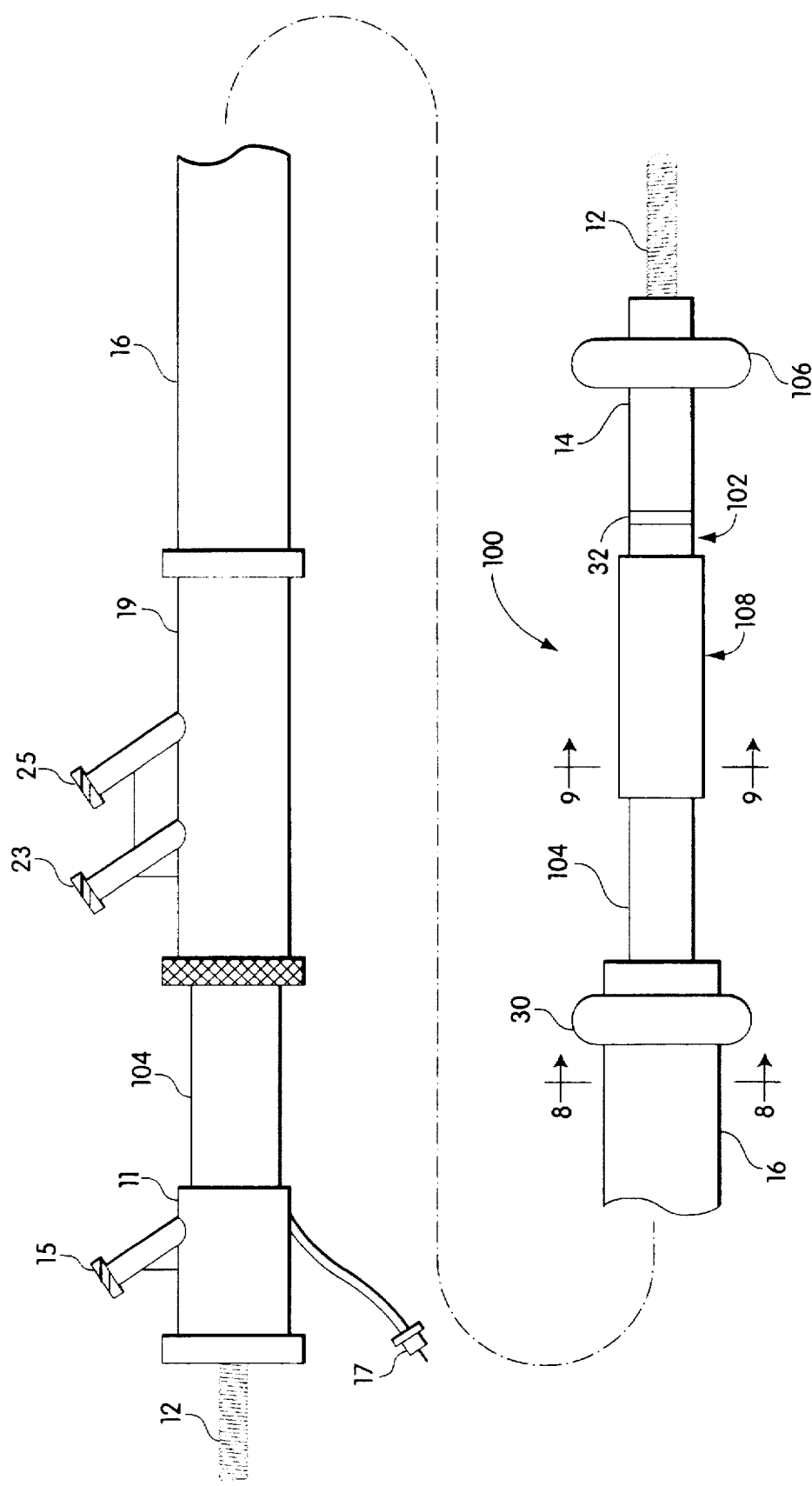
FIG. 7 is a schematic representation of one embodiment of a device for providing a polymeric barrier layer on a luminal wall.

The interfacial polymerization process can be carried out using a device such as that depicted schematically in FIG. 7. The device of FIG. 7 is substantially identical to that of FIG. 1 except that it does not include a molding balloon or molding balloon inflation lumen. Thus, the device 100 comprises three elements: a guidewire 12, a polymerization catheter 102 and a sheath 16. The guidewire is as described previously. The polymerization catheter 102 comprises an elongated tubular shaft 104 having a distal occlusion balloon 106 mounted near its distal end. An optical emitter 108 constructed in a manner substantially identical to that of the emitter in FIG. 1, is mounted on the polymerization catheter 102 in a region proximal to the distal occlusion balloon 106. One or more radiopaque markers 32 can optionally be positioned at various locations on the shaft 104. The sheath 16 includes a lumen having a diameter sufficiently large to enable passage of the polymerization catheter when the distal occlusion balloon 106 is deflated. A proximal occlusion balloon 30 is mounted at or near the distal end of the sheath.

Figure 8:
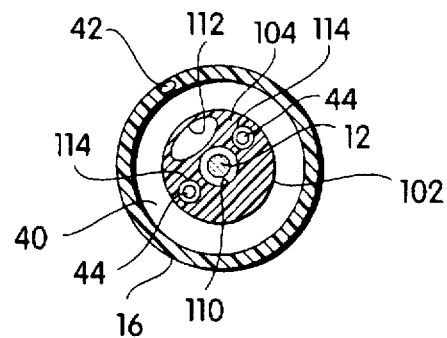
FIG. 8 is a cross-sectional view through line 8—8 of FIG. 7 at a location proximal to a proximal occlusion balloon.

As may be seen in FIG. 8, sheath 16 includes a proximal occlusion balloon lumen 42 which communicates with the interior of the proximal occlusion balloon 30 and allows it to be inflated. Shaft 104 of the polymerization catheter 102 includes multiple lumens extending from its proximal end. A central lumen 110 provides a space through which the guidewire 12 may be passed. A distal occlusion balloon lumen 112 communicates with the interior of the distal occlusion balloon 106, thereby allowing that balloon to be inflated. As also shown in FIG. 8, the sheath 16 surrounds the polymerization catheter 102 and provides an annular space 40 through which a prepolymer fluid may be injected into a treatment space positioned between the proximal 30 and distal 106 occlusion balloons. The catheter shaft 104 can further include at least one optical fiber lumen 114 through which at least one optical fiber 44 may pass, or in the alternative, the fiber may pass through the annular space 40 between the sheath and the polymerization catheter, or within the distal inflation lumen 112. In general, the optical fiber and emitter may be placed within any lumen. Moreover, it is not required that the guidewire or optical lumens be centered in the catheter shaft. The various lumens, in this and in other embodiments, may be arranged in any suitable pattern; for example, so as to maximize the size of the various lumens within a given catheter shaft size.

Figure 9:
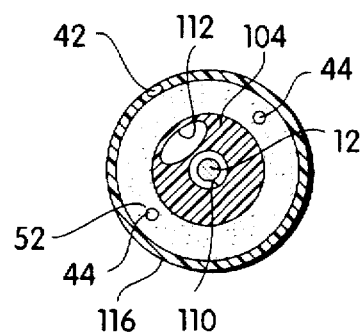
FIG. 9 is a cross-sectional view through line 9—9 of FIG. 7 across an optical emitter.

As shown in FIGS. 7 and 9, an optical emitter 108 positioned on the polymerization catheter shaft 104 comprises a flexible, translucent tube 116 containing a light scattering filler 52 of the type described earlier. One or more optical fibers 44 have distal ends terminating in the light scattering filler 52. As before, a reflective coating may be formed on the shaft 104 contained within the emitter 108. The material of construction for each of the occlusion balloons, the sheath, the polymerization catheter, and the optical emitter are as described above.

In use, the proximal and distal occlusion balloons are deflated and the sheath is extended over the polymerization catheter to a point proximal to the distal end of the polymerization catheter. The polymerization catheter with the distal occlusion balloon is guided over the guidewire to position the distal occlusion balloon at the distal end of the treatment site. The sheath is then positioned to place the proximal occlusion balloon at a desired proximal location. The proximal occlusion balloon is inflated to occlude the proximal end of the treatment site, and a flushing solution, as described previously, is injected through the annular space between the sheath and the polymerization catheter to flush blood and other biological fluids from the treatment site. Following flushing, a photoinitiator is injected through the annular space to coat and/or adsorb into tissue at the interior surface of the body lumen. Optionally, the unbound photoinitiator may be removed by flush. Then a prepolymer solution is injected into the treatment space between the proximal and distal occlusion balloons, which may displace the photoinitiator, and the distal occlusion balloon is inflated. As before, if the device is provided with a "flushing" lumen or a "valve-occlusion" balloon (described below), the distal occlusion balloon can be inflated earlier. In that case, fluid in the treatment space displaced by subsequent fluids would be displaced and removed through the "flushing" lumen. Once the prepolymer material fills the treatment space, light is directed through the optical fibers to the optical emitter and is caused to radiate therefrom in a substantially uniform radial, circumferential manner. Light which reaches the photoinitiator coating on the interior of the body lumen causes the prepolymer solution at the interface of the luminal wall to become photopolymerized, thereby forming a thin polymeric barrier layer on the luminal surface. The barrier layer "grows" outwardly into the lumen with continued illumination time. Unpolymerized material may then be flushed or aspirated from the treatment site. The balloons are then deflated and the device is withdrawn, leaving a thin barrier layer of polymeric material on the surface of the luminal wall. As used herein, the term "barrier layer" is meant to define, generally, a polymer layer that isolates a region of tissue. However, this term is meant to include also polymeric material which contacts tissue to provide structural support, to deliver pharmaceutical agents, and the like, where a continuous barrier is not necessarily formed.

Numerous variations such as those described in connection with the thick gel device are contemplated as well. For example, either one or both of the distal and proximal occlusion balloons may be eliminated and the various embodiments of the emitter may be substituted. Similarly, rather than having a multi-component device, each of the proximal and distal occlusion balloons, and the emitter, in their various combinations, may be mounted on a single multi-lumen shaft. In a preferred embodiment, at least one additional lumen is provided for introduction of a photoinitiator, a flushing solution, and/or prepolymer. If the single shaft embodiment is used, the ability to tailor the size of the treatment space is lost. However, the simplicity to vary the single shaft device overcomes the inability to vary the treatment space length for many applications. Likewise, the device may be used to withdraw flushing liquid in the manner described previously. Thus, it is intended that the numerous variations on the device described with respect to FIGS. 1–6 can be incorporated into the devices for application of thin interfacial gels as well.

Figure 10:
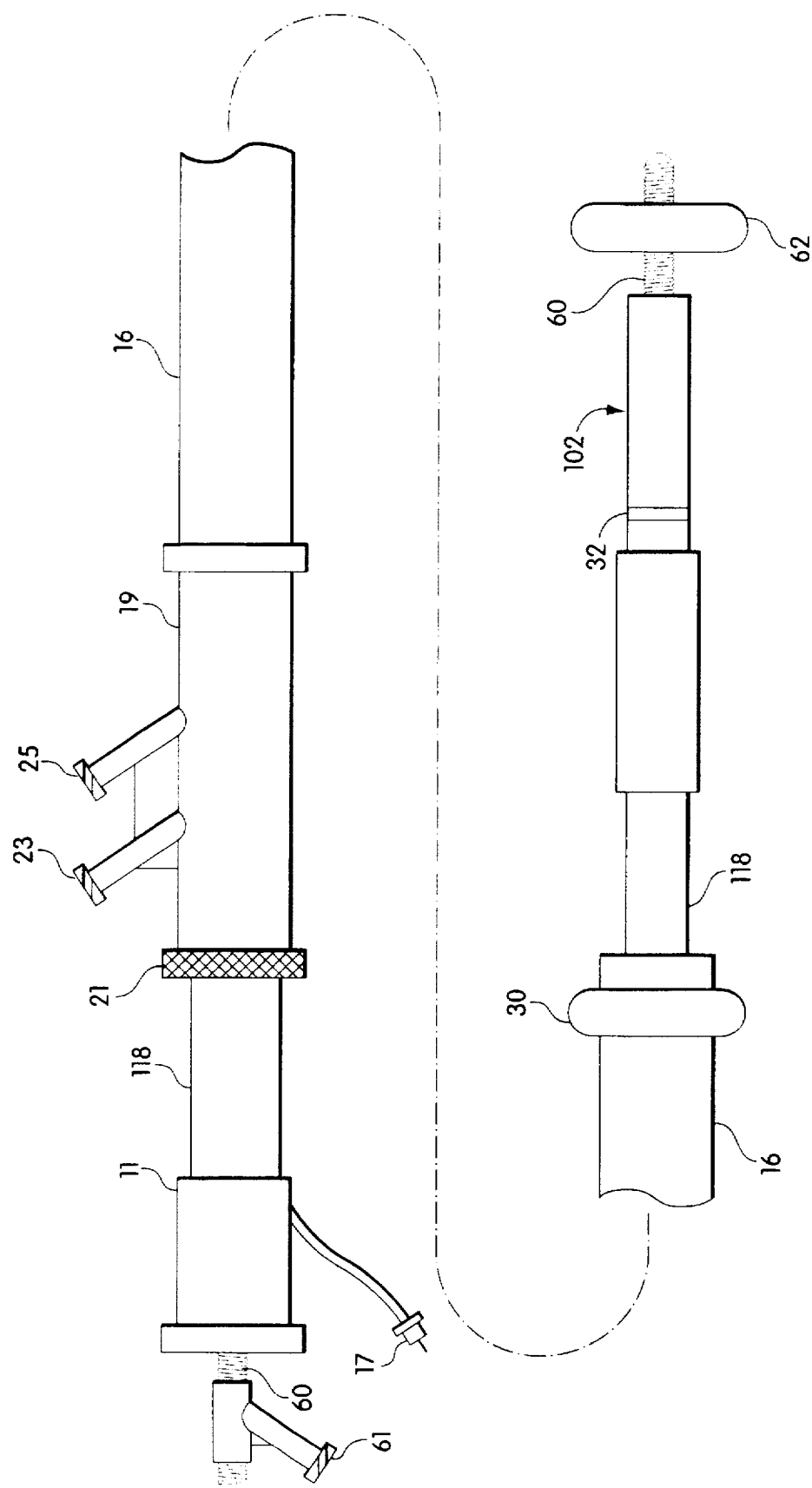
FIG. 10 is a schematic representation of a second embodiment of a device for providing a polymeric barrier layer on a luminal wall.

Another embodiment of the device is depicted schematically in FIG. 10. Although similar to the device of FIG. 7 in many aspects, the device of FIG. 10 differs in that the distal occlusion balloon is positioned on the guidewire rather than on the balloon catheter shaft in the region distal to the molding balloon. Thus, as in the thick gel embodiment, the device comprises a guidewire 60 having a distal occlusion balloon 62 mounted at its distal end. The polymerization catheter 118 is identical to that described previously with the exception that it does not include the distal occlusion balloon 62 or its related lumen. In all other aspects, the emitter 108, the sheath 16, the proximal occlusion balloon 30 and the marker 32 are identical to those described earlier. The proximal end of the device of FIG. 10 is similar to that of FIG. 4 with the exception that hub 11 does not include a molding balloon inflation port.

The method of operation of the device of FIG. 10 is substantially the same as that for the device depicted in FIG. 7. In particular, the proximal 30 and distal 62 occlusion balloons are deflated and the guidewire is navigated across a treatment site to position the distal occlusion balloon at the distal end of the treatment site. The polymerization catheter 118 is then advanced to position the emitter 108 at the treatment site. Subsequently, the sheath 16 is positioned to place the proximal occlusion balloon 30 at the proximal end of the treatment site. The proximal and distal occlusion balloons are then inflated, either simultaneously or sequentially in the same manner as described previously. The treatment site is then optionally flushed, coated with a photoinitiator, contacted with a prepolymer solution, and subjected to interfacial polymerization in the manner described above. Upon formation of the thin polymeric barrier layer on the luminal surface, the balloons are deflated and the device is withdrawn, leaving the polymeric barrier in place.

Still another embodiment of the present invention is depicted schematically FIGS. 11A and 11B. The device depicted in FIGS. 11A and 11B differs from the device of FIG. 7 in that a separate optical emitter 90 is used to provide light for the interfacial polymerization. Thus, the device of FIG. 11A includes a guidewire 12, a treatment catheter 120 having a distal occlusion balloon 106 at its distal end and a sheath 16 having a proximal occlusion balloon 30 positioned at or near its distal end. The treatment catheter 120 is transparent or translucent to the photopolymerizing light at least in the region that becomes exposed between the proximal and distal occlusion balloons. The proximal end of the device is similar to that of FIG. 7 with the exception of the optical fiber connector which is absent in the embodiment of FIG. 11A.

In use, typically post-angioplasty, the angioplasty guidewire is left in position across a treatment location. The proximal and distal occlusion balloons are deflated and the treatment catheter 120 is advanced distally to position the distal occlusion balloon at a location near the distal end of the treatment site. The sheath is then positioned over the guidewire to place the proximal occlusion balloon proximally adjacent to the treatment site. The proximal occlusion balloon is inflated and the treatment space is optionally flushed and coated with a photoinitiator in the manner described previously. The guidewire is withdrawn, and the optical emitter is then guided through the central lumen to position emitter tube 92 within the treatment space. A prepolymer solution is injected into the space between the proximal and distal occlusion balloons and the distal occlusion balloon is inflated. The prepolymer then is irradiated with light from the optical emitter in the manner described previously. The resulting polymerized layer comprises a thin barrier layer of polymeric material on the luminal surface. The balloons are deflated and the device is withdrawn, thereby leaving the polymeric barrier in position on the luminal wall.

In each of the embodiments described herein, the treatment space is defined as that region between proximal and distal occlusion balloons which are inflated to isolate a segment of the vessel. It has also been noted that the proximal and distal occlusion balloons can each be of generally the same shape and material. In an alternative embodiment, applicable to each of the devices described above, one of the balloons, preferably the distal occlusion balloon, may be underinflated, fabricated of a particular material, or formed in a particular shape and/or size such that it is provided with a lesser ability to effectively occlude the lumen. Such a configuration offers certain advantages in that the resulting balloon can occlude the vessel while also allowing fluids injected into the treatment space to flow distally beyond the device. Balloons which offer the ability to occlude the lumen and allow some fluid to exit the treatment space during a fluid injection are referred to herein as "valve-occlusion" balloons. A valve-occlusion balloon can act, in part, as a one-way valve by allowing excess fluid delivered between the balloons to exit from the treatment space in a region that opens between the periphery of the balloon and the lumen wall during enhanced pressure conditions that occur when fluids are injected into the treatment space. As a result, fluid is allowed to flow beyond the treatment space, thereby alleviating the need for aspirating fluid proximally and limiting hydrostatic intramural chamber pressure without any retrograde flow or seepage of blood to the isolated segment.

Figure 12A:
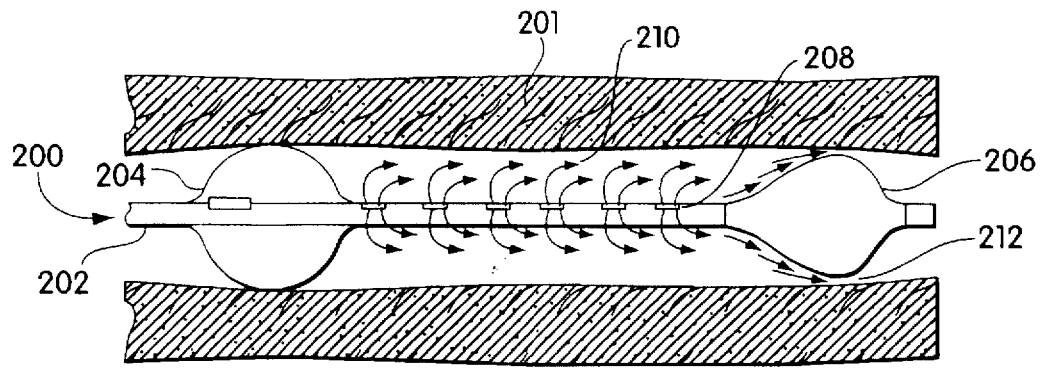
FIGS. 12A and 12B are schematic representations of a device having a valve-occlusion balloon.
Figure 12B:
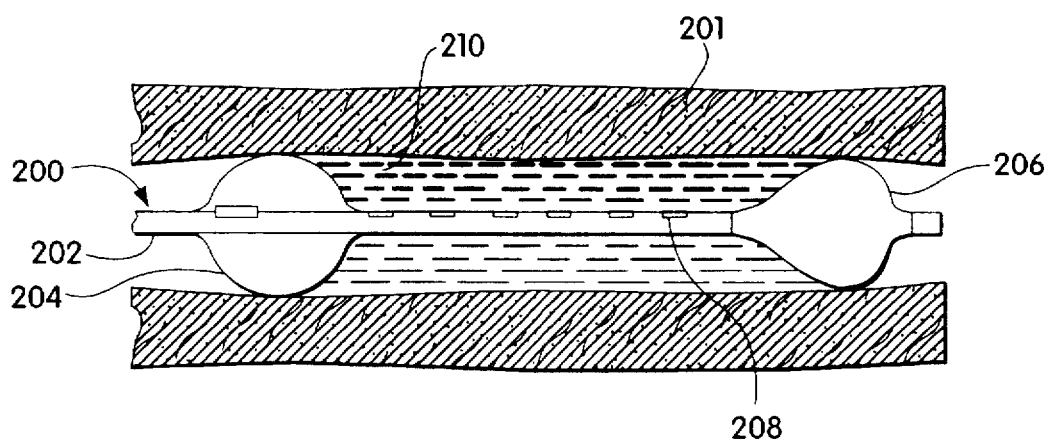

A catheter device including a valve-occlusion balloon is illustrated in FIGS. 12A and 12B. Referring first to FIG. 12A, the distal end of catheter device 200 is positioned within a blood vessel 201. The device comprises a catheter shaft 202 having proximal 204 and distal 206 occlusion balloons longitudinally spaced apart near the distal end of the catheter shaft 202. Unlike the devices described above, in which fluids are injected into the treatment space via an annular space formed between a sheath and a catheter, in the exemplary device of FIGS. 12A and 12B, the sheath has been eliminated and the proximal occlusion balloon 204 is mounted directly on the catheter shaft 202. Fluids 210 are injected into the treatment space through one or more ports 208 positioned on the catheter shaft between the occlusion balloons. The ports communicate with at least one lumen in the catheter shaft through which the fluids 210 can be injected. In this and other embodiments of the invention in which a port provides fluid communication between a lumen within a shaft and a region outside of the shaft, for example ports 208 providing fluid communication between a lumen within shaft 202 and the treatment space defined by occlusion balloons 204 and 206, the port or ports may be formed by shaving, or skiving, an exterior wall of the shaft to open the lumen.

As can be seen in FIG. 12A, a fluid 210 injected into the treatment space (and/or fluid in the treatment space displaced by fluid 210) is allowed to flow past the distal, valve-occlusion balloon 206 about the periphery 212 of that balloon when fluid pressure within the treatment space is sufficient. At the same time, the proximal balloon 204 occludes the proximal end of the treatment space and prevents fluid flow in the proximal direction. As shown in FIG. 12B, upon termination of injection of the fluid 210 into the treatment space, the distal occlusion balloon 206 reseals the distal end of the treatment space and contains the fluid injected therein.

Valve-occlusion balloon 206 can be formed in various ways. For example, it can be formed using a material that is more compliant than that from which occlusion balloon 204 is formed. Alternatively, both balloons may be manufactured of the same material, however valve-occlusion balloon 206 may be formed with a wall thickness that is less than that of occlusion balloon 204 to thereby render it more flexible. If the balloons are independently inflatable, valve-occlusion balloon 206 may be created by inflation to a lower pressure than that used to inflate occlusion balloon 204. A check valve or the like may be used to achieve underinflation of one balloon relative to the other. Alternatively still, valve-occlusion balloon 206 can have a shape that allows an increase in pressure in the treatment space between the balloons to facilitate removal of fluid from the treatment space past the valve-occlusion balloon. For example, valve-occlusion balloon 206 may be of a different shape and/or size relative to occlusion balloon 204 so that the area of contact between valve-occlusion balloon 206 and the interior wall of vessel 201 is smaller than the area of contact between balloon 204 and the interior wall of the vessel 201.

By eliminating the need for a separate drain lumen, the valve-occlusion balloon allows a catheter shaft of the same outer diameter to have a larger central, injection or guidewire lumen, or smaller catheter shaft, than would otherwise be possible. Likewise, if the device is intended to allow blood perfusion during the treatment procedure, the central lumen can be used for blood flow, thereby allowing a higher rate of flow through the catheter than would be possible if a separate drain lumen were required.

Figure 13A:
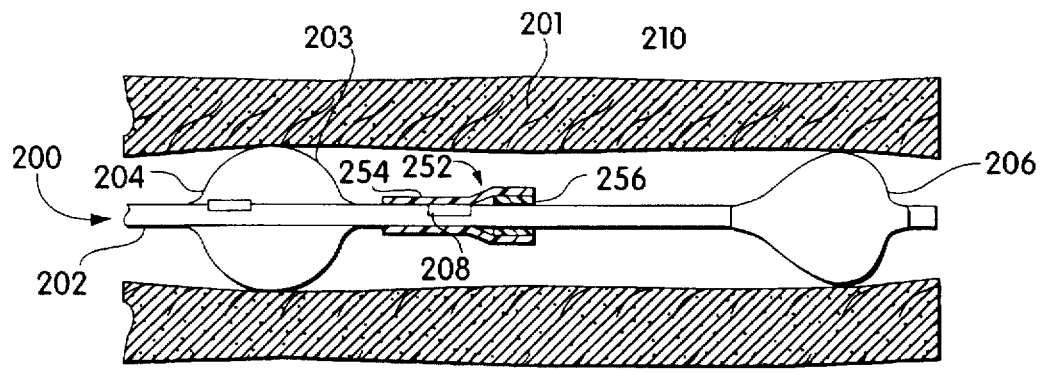
FIGS. 13A and 13B are schematic representations of a device having a flow-directing baffle.
Figure 13B:
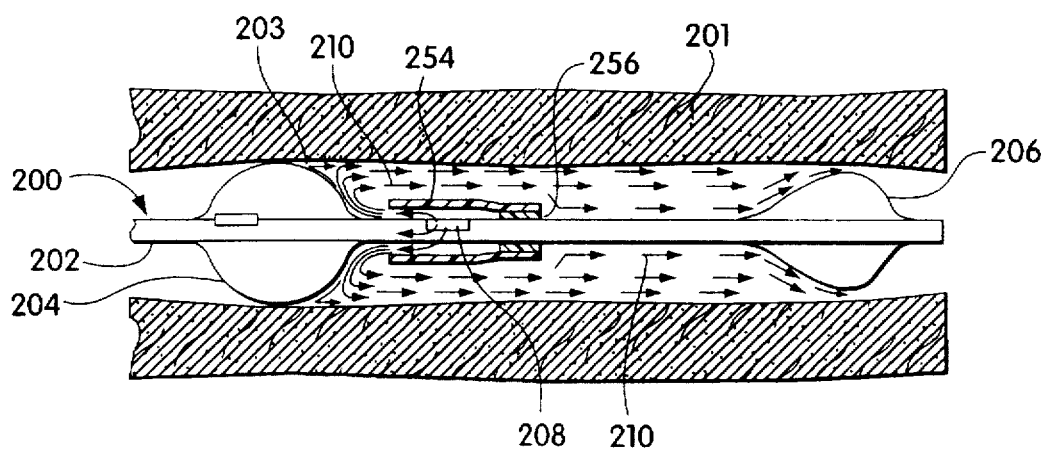

Infusion of a flushing fluid into a treatment space defined by two occluding balloons, as described above with reference to FIGS. 12A and 12B, following introduction of the photoinitiator or prepolymer may, in some circumstances, fail to completely flush the treatment space. With reference to FIG. 13A, this may result in unwanted residual material at the proximal end 203 of the treatment space adjacent proximal occlusion balloon 204. This effect can be eliminated by providing a baffle 252 on the catheter shaft 202 to direct fluid injected into the treatment space toward the proximal occlusion balloon 204 to thereby provide sufficient mixing and flushing at the proximal end of the treatment space. In this embodiment, baffle 252 comprises an elastic sheath 254 which surrounds the catheter shaft 202 in the region of an injection port 208 and is secured to the catheter shaft by an adhesive 256 at a location distal to the injection port 208. As is shown in FIG. 13B, fluid 210 exiting the injection port expands the elastic sheath 254 and is caused to flow proximally in the treatment space toward the proximal occlusion balloon 204. The proximal fluid flow removes residual material positioned at the proximal end 203 of the treatment space adjacent to the proximal occlusion balloon. Upon reaching the proximal end of the treatment space, the fluid begins a distal flow through the entire treatment space and ultimately flows beyond a distally-positioned valve-occlusion balloon 206. Fluid exiting from the injection port 208 is prevented from flowing immediately in the distal direction by the adhesive 256 which is used to secure the elastic sheath 254 to the shaft, effectively creating a barrier. Upon completion of the fluid injection, the elastic sheath 254 retracts about the injection port 208 and catheter shaft 202 into the configuration shown in FIG. 13A to prevent fluid in the treatment space from retrograde flow into the catheter shaft via the injection port. Thus, while acting as a baffle to direct injected fluid toward the proximal occlusion balloon, the elastic sheath also acts as a one-way check valve to prevent unwanted fluid flow back into the injection port.

In this and in other embodiments described herein in which fluid is caused to flow out of a port, the rate of fluid flow out of injection port 208 and into the treatment space between the occlusion balloons may be increased by blocking a lumen in shaft 202, through which the fluid passes, just distal to the port. For example, quick-setting adhesive or silicone may be injected into the lumen just distal to the port so that all fluid flow is directed into the treatment space.

Figure 14:
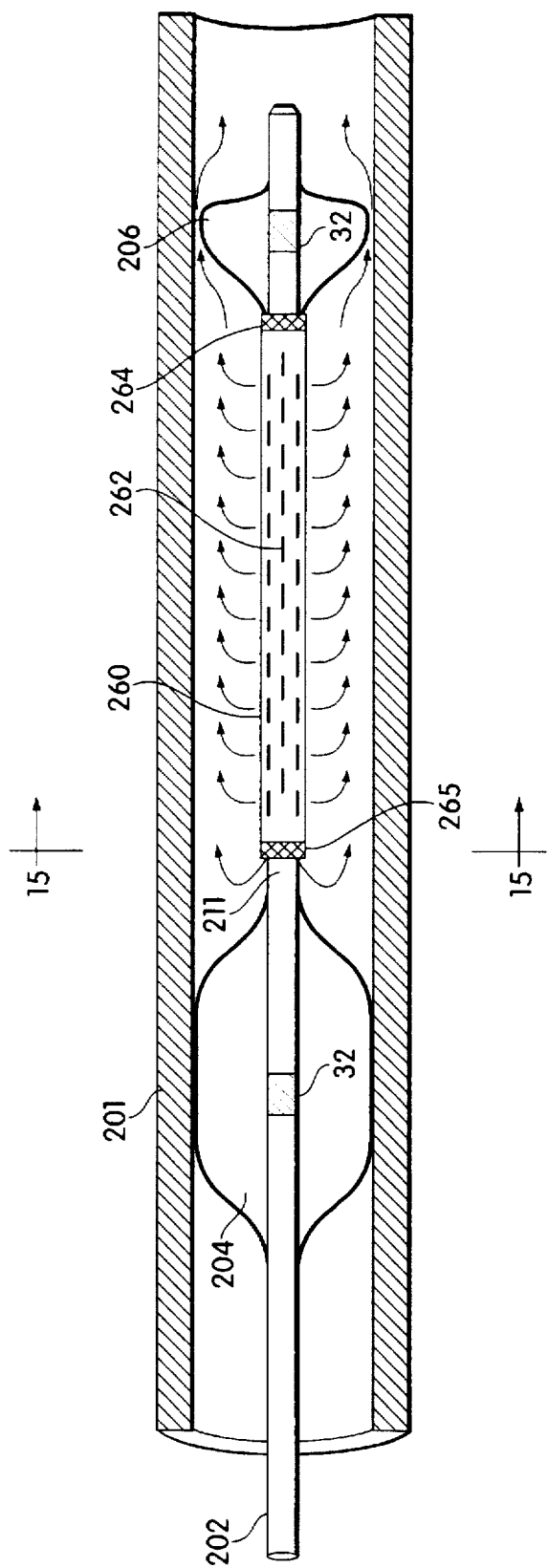
FIG. 14 is a schematic representation of a device including a flushing sleeve and a valve-occlusion balloon.

The present invention also provides a device for flushing a surface of a body lumen or cavity with a fluid. Referring to FIG. 14, a distal end of a catheter including such a device is illustrated that includes a shaft having a distal end insertable into the lumen or cavity, a proximal end that remains outside of the lumen or cavity, and a perforated flushing sleeve 260 surrounding a portion of the distal end of the shaft. The perforated flushing sleeve includes an interior that is connected to a source of fluid to be ejected into the lumen or cavity, and is positioned at a portion of the shaft that can be placed adjacent portions of the lumen or cavity that desirably are treated with the fluid. For example, the flushing sleeve can surround a portion of the shaft that includes one or more fluid ejection ports so as to facilitate delivery of the fluid from the ejection ports into the lumen or cavity via the perforations.

According to a preferred embodiment, the flushing sleeve is used in conjunction with a catheter device described hereinabove and illustrated in FIGS. 13A and 13B, for injection of a photoinitiator, prepolymer fluid, flushing fluid, etc. into an occluded region of a body lumen or cavity such as a blood vessel. It is to be understood, however, that the flushing sleeve can be used on any such device where it is desirable to introduce into a body lumen or cavity any fluid such as a therapeutic agent or the like.

Flushing sleeve 260 can be made of any material suitable for use in an environment in which it will be used, such as stainless steel, rigid polymeric material, elastomer, or the like. When made of a relatively rigid material, it can be made to have an inner diameter slightly larger than the exterior diameter of the shaft to provide for fluid flow between the shaft and the sleeve. When made of a flexible material such as an elastomer, the sleeve can have an interior, unstretched diameter less than the exterior of the shaft, or the interior diameter can be equal to or slightly larger than the exterior diameter of the shaft. According to preferred embodiments, the flushing sleeve is made of elastic tubing which is slightly larger in inner diameter than the outer diameter of the shaft 202 of the catheter. Sleeve 260 can be optically clear, or can include light scattering or absorbing characteristics that may be desirable in a particular application, including uneven distribution of light scattering and absorbing characteristics for "shadowing" of electromagnetic radiation directed through the sleeve.

Flushing sleeve 260 includes perforations, or distribution ports 262 through which fluid is delivered to the lumen or cavity. Distribution ports 262 can be provided in any number, and in a variety of sizes and shapes, and can be distributed evenly or unevenly on the sheath. Preferably, distribution ports 262 are distributed evenly around the entire circumference and length of the flushing sleeve, and number for example from 50 to 100. A convenient way of making such distribution ports in an elastomeric sleeve 260 is as slits, by the use of a beveled hypodermic needle, which produces slits about 0.25 mm. long. Axial orientation of the slits, as illustrated, is preferred. Other sizes, shapes, and orientations of distribution ports can be provided.

According to the embodiment illustrated, the elastomeric tubing that defines flushing sleeve 260 is advanced over a section of the catheter distal to proximal occlusion balloon 204 and proximal to distal occlusion balloon 206, thereby covering one or more ports (not illustrated) from a lumen of the catheter leading into the occlusion zone. Flushing sleeve 260 can be immobilized on shaft 202 in one of several ways. For example, sleeve 260 can be attached to shaft 202 via heat sealing or use of adhesive at one or both ends thereof, and/or at one or more locations along the length of the sleeve. In this way, either or both of the ends of the sleeve can be completely sealed circumferentially around the shaft, or one or both can be left unsealed to the shaft to allow fluid to emanate from between the exterior of the shaft and the interior of the sleeve. Alternatively, one end (or both ends) of the sleeve can be joined to the catheter shaft while at least one passage 266 (FIG. 15, not shown in FIG. 14) is maintained between the sleeve and the shaft at the end that is joined. The passage(s) 266 is kept patent by suitable means.

According to a particularly preferred embodiment, a further improvement in fluid distribution can be achieved by combining the functions of a flushing sleeve and a flow baffle. The combination of these elements both flushes potential static regions, and provides mixing throughout the treatment zone between the occluding balloons. According to this embodiment, illustrated in FIGS. 14–16, the distal end 264 of flushing sleeve 260 is completely sealed to shaft 202 via adhesive, and the proximal end 265 of the sleeve is sealed to the shaft via adhesive while one or more fluid passages 266 are maintained between the shaft and the sleeve at proximal end 265. Fluid passages 266 are shown in more detail in FIG. 15. One convenient mechanism for providing fluid passages 266 is the insertion of small fluoropolymer-coated plugs, for example about 0.010 inch (0.25 mm) in diameter, between shaft 202 and sleeve 260 which locally prevent adherence of the sheath and the shaft, and which are removed after the bond is set leaving suitable flushing ports. As noted, it is also possible to create axial flushing by leaving one or both ends of the flushing sheath unbonded to the shaft. Other options in construction of a flushing sheath include having flushing ports at both ends, or having a flushing port at least at one end which operates as shown in FIGS. 13A and 13B.

In operation, the fluid to be injected into the treatment space between occlusion balloons 204 and 206 is applied under pressure to the interior of the flushing sleeve through one or more injection ports (not illustrated) on the shaft under the flushing sleeve 260, into the fluid delivery lumen. The pressure slightly expands sleeve 260, and thereby opens the perforations, or distribution ports, 262 of the sleeve, providing direct flow of the fluid in a radial direction away from the shaft and sleeve. Fluid under pressure also emerges from the fluid passages 266 (or from between the sleeve and the shaft if an end of the sleeve is not adhered to the shaft), providing the desired axial flushing action in the vicinity of the proximal balloon (and/or the distal balloon). To achieve both effects simultaneously, the ratios of the clearance of the injection port(s) in the shaft, the size and number of the distribution ports 262, and the diameter of the fluid passages 266 desirably are appropriately sized for a particular range of operating pressure and a particular sleeve compliance. The required adjustments are readily achieved by inspecting the flow patterns of dyed liquids ejected through prototype devices in clear tubes similar in size to the particular body lumen or cavity desirably treated.

Figure 16:
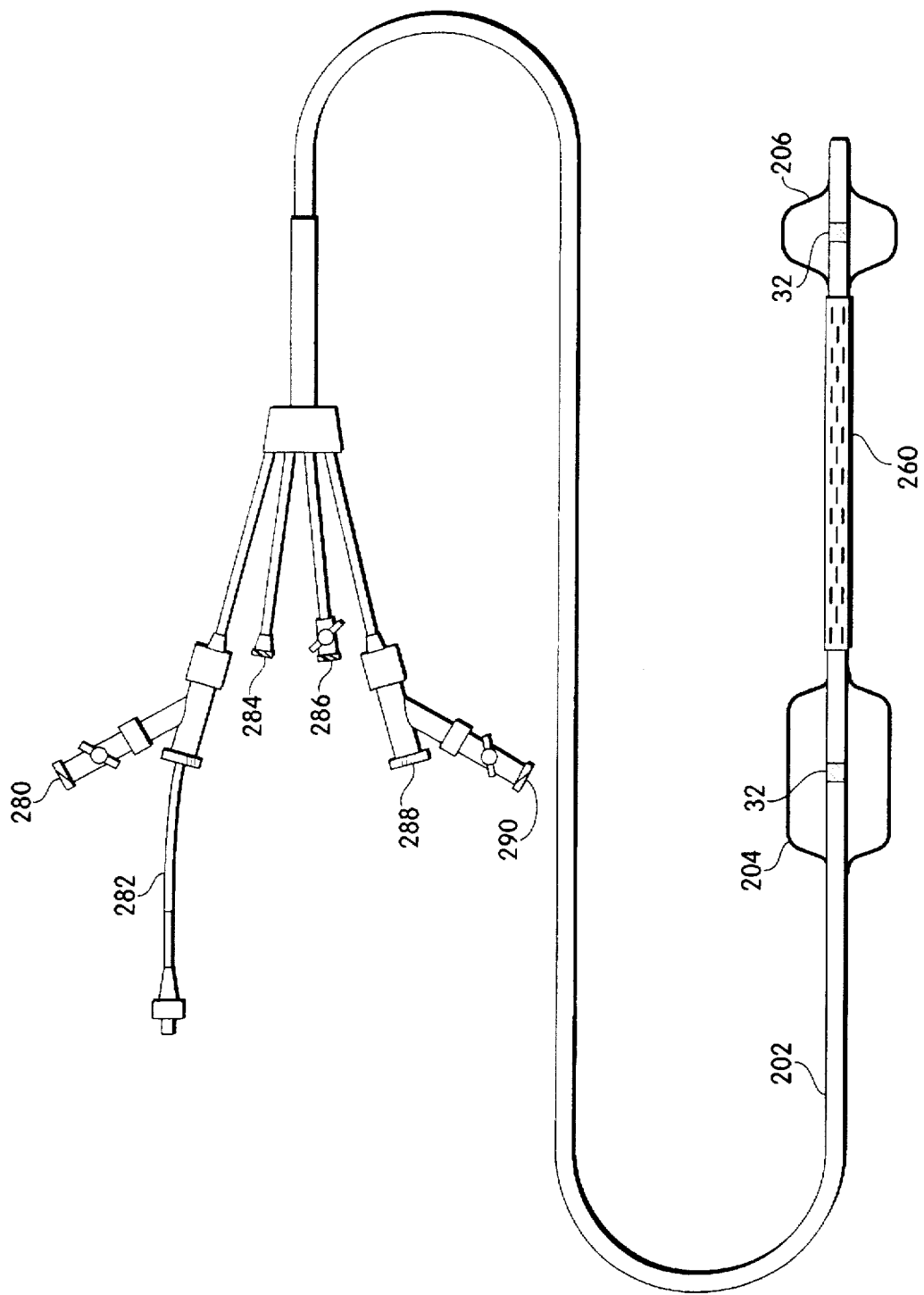
FIG. 16 is a schematic representation of the device illustrated in FIG. 14, including an arrangement of orifices at the proximal end of the device for accessing various lumens and passageways of the device.

A schematic view of a catheter including a flushing sleeve according to one embodiment of the invention is shown in FIG. 16. At the distal end, the flushing sleeve 260 is shown between the proximal 204 and distal 206 occlusion balloons, all mounted on the catheter shaft 202 which carries radio-opaque markers 32. At the proximal end, an arrangement of orifices according to one embodiment is illustrated: a proximal balloon control port 280, a connection to an optical fiber 282, a solution injection and flushing port 284, a distal balloon control port 286, a port 288 for a guidewire lumen, and a connector 290 for flushing the guidewire lumen.

Figure 15:
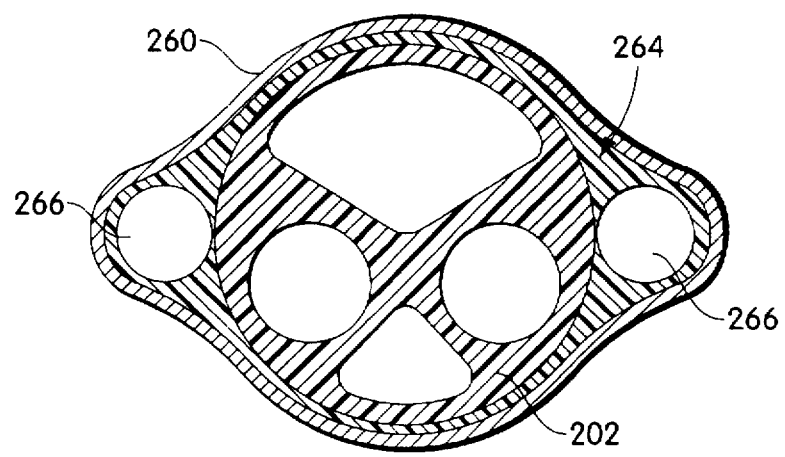
FIG. 15 is a cross-sectional view through line 15—15 of FIG. 14.

The present invention also provides methods of directionally-controlled application of fluid to the interior surface of a body lumen or cavity, which methods can be carried out with the aid of, for example, the flow-directing baffle 254 described above with reference to FIGS. 13A and 13B, the flushing sleeve 260 described with reference to FIGS. 14–16, and/or a preferred embodiment of the flushing sleeve that incorporates axially-directed fluid flow (provided via the principle of the baffle 254 or fluid passages 266). The fluid that is applied according to the methods can be a flushing liquid that optionally contains a pharmaceutical or therapeutic agent, a photoinitiator, a prepolymer fluid, saline solution, or other fluids described herein or that are within the purview of those of ordinary skill in the art. According to one aspect, a method is provided that involves providing a fluid to such an interior surface by occluding the lumen or cavity with an occlusion element, and directing pressurized fluid toward the occlusion element so as to flush a region defined by the occlusion element and the surface of the lumen or cavity. According to another aspect, a method involves, in a lumen or elongated cavity having an axis of elongation, directing fluid in a first direction toward the surface of the lumen or cavity and simultaneously directing fluid within the lumen or cavity in a second direction perpendicular to the first direction. According to one embodiment, the first direction is from the center of the lumen or cavity radially outward, and the second direction is in an axial direction in the lumen or cavity.

As used herein, "directing" is meant to define flowing, spraying, or otherwise providing fluid under pressure into the lumen or cavity in a predetermined direction from a source provided in the lumen or cavity. The methods described also can involve occluding a region of the lumen or cavity, for example with one or more occlusion elements such as balloons, and can involve allowing the fluid to escape from the occluded region past one occlusion balloon preferentially, as described above with reference to FIGS. 12A and 12B. If the fluid is a prepolymer fluid, the methods can involve exposing the prepolymer fluid to electromagnetic radiation after providing the fluid in the cavity or lumen, for a period of time sufficient to partially or fully polymerize the fluid.

The improved fluid distribution in the treatment zone which is obtained by use of a flushing sleeve as described above is useful in all circumstances, because of its improved speed and thoroughness of mixing. The improvement is especially advantageous when the treatment zone has other egress routes in addition to a valve balloon; for example, a sidebranch in an artery. With a non-distributed flushing mechanism, as described in prior art drug delivery catheters, the injection of a new fluid into the treatment space is normally uneven, because of flow down the sidebranch, and the distal portion of the treatment zone may be static and experience very little exchange of fluid. Any treatment will therefore be uneven. Such effects are readily observed in a simulated system. The improvement given by a flushing sheath as described, or a functionally similar device, can be observed in native arteries either by staining patterns of dye on the artery wall, or by the uniformity and completeness of polymer layers created on the wall of the lumen. Although the desirability of thorough distribution has been recognized in other contexts, previous dual-balloon type drug delivery catheters employing a treatment zone have not made careful provision for evenness of distribution of therapeutic agent within the zone.

In accordance with any of the embodiments described herein, if photoinitiator is rapidly adherent to the interior lumen tissue wall, then the interior surface may be prestained with photoinitiator before insertion of the device. For example, an artery may be flushed with normal saline, followed by photoinitiator dye in saline. Blood (or other local body fluid) then is allowed to flow while the device is being inserted and located at the treatment site. Although large areas of the vessel wall are stained with photoinitiator according to the method, only at the treatment site defined by the occlusion balloons are both prepolymer and light simultaneously present, thus localizing the creation of a barrier polymer layer.

As noted above, the molding and occlusion elements need not be limited to radially expandable balloons. Rather, occlusion can be achieved using other radially expandable structures. Alternatively, in a lumen having a decreasing diameter in the distal direction, distal occlusion may be achieved by advancing the distal tip of the device until it contacts the lumen walls in a region of decreased diameter.

In the embodiments above, the applied polymer layer has been presented as essentially annular. However, in some circumstances it may be desirable to make a layer which does not entirely cover the inner circumference of the vessel. For example, in any artery, it may be necessary to avoid a major side branch. Non-annular coatings can also be produced by catheters of the invention with minor modifications. For example, the molding balloon, when used, can be eccentric, so that prepolymer is not present on one side of the vessel. Alternatively, light can be prevented from passing through one or more sectors of the balloon or the catheter shaft, thereby preventing crosslinking of polymer in a particular zone. In order to properly position the non-coated zone, the catheter shaft should be provided with means for visualizing its radial orientation within the vessel or lumen. For example, a longitudinal strip of radio-opaque material —optionally also light-opaque —could be mounted on the catheter in the appropriate place.

Equivalents

Although specific features of the invention are included in some embodiments and drawings and not others, it should be noted that certain features may be combined with other features in accordance with the invention.

In addition, it should be noted that the invention is not intended to be limited to the specific materials and construction described herein.

It should be understood that the foregoing description of the invention is intended to be merely illustrative thereof, that the illustrative embodiments are presented by way of example only, and that other modifications, embodiments, and equivalents may be apparent to those skilled in the art without departing from its spirit.

Having thus described the invention, what we desire to claim and secure by Letters Patent is:

1. A device for delivery of a therapeutic agent to a body cavity or lumen, comprising:
   one or more elongated shafts, each with a proximal end, and a distal portion adapted for insertion into a body lumen or cavity;
   at least one occlusion element mounted on one or more of the shafts;
   at least one injection lumen in at least one shaft, suitable for injection of an agent into a treatment space defined at least at one end by the occlusion element, wherein said injection lumen communicates with at least one injection port located on the shaft; and
   a flushing sleeve mounted about the injection port, and arranged on the shaft so as to create at least one axially-directed flushing port.

2. A device as in claim 1, comprising at least two shafts that are concentric and are movable with respect to each other.

3. A device as in claim 1, comprising two occlusion elements.

4. A device as in claim 1, wherein the flushing sleeve comprises a tube with multiple radial distribution points in its surface, arranged on the shaft so as to create at least one radially-directed flushing port.

5. A device as in claim 1, wherein the at least one occlusion element is an inflatable balloon.

6. A device as in claim 1, further comprising, in fluid communication with the distal portion of the shaft, a solution containing at least one pharmaceutical agent for infusion into the treatment space.

7. A device as in claim 1, wherein the device includes a proximal occlusion element and a distal occlusion element that define therebetween the treatment space, one of the elements comprising a valve-occlusion balloon.

8. A device as in claim 1, wherein the flushing sleeve has an end that is affixed to the shaft so as to create an axially-directed flushing port.

9. A device as in claim 1, wherein the flushing sleeve is elastomeric.

10. A device as in claim 1, further comprising a lumen for a guidewire.

11. A device as in claim 10, further comprising an occlusion element mounted on a guidewire.

12. A device as in claim 1, wherein the device further comprises a sheath covering the outer surface of the outermost shaft and moveable with respect to said shaft.

13. A device as in claim 12, further comprising an occlusion element mounted on the sheath.

14. A device as in claim 1, wherein the device includes a proximal occlusion element and a distal occlusion element that define therebetween the treatment space.

15. A device as in claim 14, wherein the proximal and distal occlusion elements are radially-expandable balloons.

16. A device as in claim 1, further comprising:
   an emitter of electromagnetic radiation associated with the shaft.

17. A device as in claim 16, wherein the emitter of electromagnetic radiation is movable axially relative to the occlusion element.

18. A device as in claim 16, wherein the emitter of electromagnetic radiation is connected via an optical fiber to a source of electromagnetic radiation near the proximal end of the shaft.

19. A device as in claim 1, further comprising a reservoir of fluid prepolymer in fluid communication with the injection lumen.

20. A device as in claim 19, wherein the prepolymer fluid is photopolymerizable upon application of electromagnetic radiation.

21. A device as in claim 19, wherein the prepolymer fluid is photopolymerizable to form a biodegradable polymeric material.

22. A device as in claim 19, further comprising a reservoir of photoinitiator in fluid communication with the distal portion of the shaft.

23. A device as in claim 1, further comprising at least one inflation lumen in the shaft, communicating with the occlusion element and with the proximal end of the shaft.

24. A device for delivery of a fluid to a body cavity or lumen, comprising:
   an elongated shaft having a proximal end, and a distal portion adapted for insertion into a body lumen or cavity; and
   a flushing sleeve mounted about an injection port on the shaft, and arranged on the shaft so as to direct at least a portion of agent ejected from the injection port axially.

25. A device as in claim 24, further comprising an emitter of electromagnetic radiation associated with the shaft.

26. A device as in claim 24, further comprising at least one injection lumen communicating with the injection port at the distal portion of the shaft, suitable for injection of a fluid into a treatment space at the distal portion of the shaft.

27. A device as in claim 26, further comprising a reservoir of therapeutic agent in communication with the injection lumen.

28. A device as in claim 26, further comprising a reservoir of photoinitiator in communication with the injection lumen.

29. A device as in claim 26, further comprising a reservoir of fluent prepolymer in communication with the injection lumen.

30. A device as in claim 26, wherein the flushing sleeve is an elastomeric sleeve having a first end and a second end, mounted about the injection port and secured to the shaft at its first end so as to direct at least a portion of fluid ejected from the injection port axially from the second end.

31. A device as in claim 30, wherein the flushing sleeve includes multiple radial distribution ports in its surface and is arranged so as to create at least one radially-directed flushing port.

32. Apparatus for treatment of a hollow organ or tissue lumen of a mammal comprising:
   an elongated shaft having a distal portion adapted to be inserted into a hollow organ or tissue lumen of a mammal during treatment and a proximal portion adapted to remain outside the mammal during treatment;
   a first occlusion element at the distal portion of the shaft adapted to occlude the hollow organ or lumen and thereby, during the treatment of the organ or lumen, to prevent fluid flow therepast while fluid pressure in the lumen or organ does not exceed a threshold value; and
   a second occlusion element at the distal region of the shaft having an essentially circular cross section when expanded, spaced from the first occlusion element, adapted to occlude the hollow organ or tissue lumen and prevent fluid flow therepast, and being constructed and arranged to withstand during treatment a second fluid pressure, less than the threshold pressure, applied within the hollow organ or tissue lumen between the first and second occlusion elements thereby preventing fluid flow therepast and to allow fluid flow therepast during treatment at the threshold fluid pressure.

33. Apparatus as in claim 32, further comprising a reservoir of therapeutic material in communication with an injection port located between the first and second occlusion elements at the distal portion of the shaft.

34. Apparatus as in claim 32, further comprising a flushing sleeve mounted about the injection port, and arranged on the shaft so as to create at least one axially-directed flushing port.

35. Apparatus of claim 32, wherein the second occlusion element is more compliant than is the first occlusion element.

36. Apparatus of claim 32, wherein the second occlusion element is shaped so as to allow fluid to flow past it more readily than the first occlusion element.

37. Apparatus as in claim 32, further comprising a reservoir of prepolymeric fluid in communication with an injection port between the first and second occlusion elements at the distal portion of the shaft.

38. Apparatus as in claim 37, further comprising a flushing sleeve mounted about the injection port, and arranged on the shaft so as to create at least one axially-directed flushing port.

39. Apparatus as in claim 32, further comprising a reservoir of photoinitiator in communication with an injection port between the first and second occlusion elements at the distal portion of the shaft.

40. Apparatus as in claim 39, further comprising a flushing sleeve mounted about the injection port, and arranged on the shaft so as to create at least one axially-directed flushing port.

41. Apparatus as in claim 32, further comprising an emitter of electromagnetic radiation associated with the shaft.

42. A device as in claim 41, wherein the emitter of electromagnetic radiation is connected via an optical fiber to a source of electromagnetic radiation near the proximal end of the shaft.

43. Apparatus as in claim 32, wherein the first and second occlusion elements comprise radially-expandable balloons.

44. Apparatus of claim 43, wherein the second occlusion element is inflated to a lesser extent than is the first occlusion element.

45. A method of applying a fluid to the interior surface of a body lumen or cavity, comprising:
   entering the lumen or cavity with a catheter having an elongated shaft that includes a distal end insertable into the lumen or cavity and a proximal end adapted to remain outside of the lumen or cavity;
   occluding the lumen or cavity with an occlusion element near the distal end of the shaft; and
   directing fluid toward the occlusion element so as to flush a region at an interface of the occlusion element and the surface of the lumen or cavity.

46. A method as in claim 45, wherein the fluid contains a therapeutic agent.

47. A method as in claim 45, wherein the fluid comprises a photoinitiator.

48. A method as in claim 45, wherein the fluid comprises a photopolymerizable prepolymer.

49. A method as in claim 45, comprising expelling the fluid from an injection port near the distal and end of the shaft and directing the fluid toward the occlusion element via a flushing sleeve having a first end and a second end, mounted about the injection port and secured to the shaft at the first end, the second end directed toward the occlusion element.

50. A method as in claim 49, wherein the sleeve is mounted between the occlusion element and a second occlusion element, and the second occlusion element is a valve-occlusion balloon.

51. A method as in claim 49, wherein the flushing sleeve comprises an elastomeric tube having multiple radial distribution ports, the method involving allowing the fluid to be directed by the sleeve axially from a space between the second end of the sleeve of the shaft toward the occlusion element, and radially through the multiple radial distribution ports.

52. A method as in claim 51, wherein the flushing sleeve is mounted between the occlusion element and a second occlusion element.

53. A method as in claim 52, wherein the second occlusion element is a valve-occlusion balloon.

54. A method of applying a fluid from an applicator to an interior surface of a body lumen or cavity having an axis of elongation, comprising:
    directing fluid in a first, radial direction from the applicator towards the surface of the body lumen or cavity and simultaneously directing fluid from the applicator within the body lumen or cavity in a second, axial direction perpendicular to the first direction.

55. A method as in claim 54, further comprising, prior to the directing step, occluding a region of the body lumen or cavity to define a treatment space, wherein the fluid is applied within the treatment space.

56. A method as in claim 54, wherein the fluid contains a therapeutic agent.

57. A method as in claim 54, involving directing the fluid from at least one injection port located between proximal and distal occlusion elements at the distal portion of a catheter shaft.

58. A method as in claim 54, wherein the fluid comprises a photoinitiator.

59. A method as in claim 54, wherein the fluid comprises a photopolymerizable prepolymer.

60. A method as in claim 54, further comprising photopolymerizing a fluid prepolymer within the body lumen or cavity.

61. A method as in claim 54, comprising directing the fluid from an injection port at a distal portion of a catheter, and allowing the fluid to be directed by a flushing sleeve mounted about the injection port.

62. A method as in claim 61, wherein the flushing sleeve comprises a tube having a first end and a second end and multiple radial distribution ports, the sleeve being affixed to the catheter shaft at its first end, the method involving allowing the fluid to be directed by the sleeve axially from a space between the second end of the sleeve and the shaft, and radially through the multiple radial distribution ports.

63. A method as in claim 62, wherein the sleeve is elastomeric.

64. A method of applying a fluid to the interior surface of a body lumen or cavity, comprising:
    occluding a diseased region of a hollow organ or tissue lumen of a mammal by positioning a first occlusion element in the hollow organ or lumen and positioning a second occlusion element, spaced from the first occlusion element, in the hollow organ or lumen, thereby defining a treatment space including the diseased region isolated by the occlusion elements;
    applying fluid to the occluded region;
    increasing pressure of the fluid; and
    allowing the pressurized fluid to escape from the occluded region past the second occlusion element, while preventing the fluid from escaping past the first occlusion element.

65. The method of claim 64, wherein at least one of the occlusion elements comprises an inflatable balloon.

66. The method of claim 64, wherein the fluid contains a therapeutic agent.

67. The method of claim 64, wherein the fluid comprises a photoinitiator.

68. The method of claim 64, wherein the fluid is a fluent prepolymer, the method further comprising photopolymerizing the fluent prepolymer at the diseased region of the hollow organ or tissue lumen.

69. The method of claim 64, wherein the first and second occlusion elements are radially-expandable balloons.

70. The method of claim 69, wherein the second occlusion element is inflated to a lesser extent than is the first occlusion element.

71. The method of claim 69, wherein the second occlusion element is more compliant than is the first occlusion element.

72. The method of claim 69, wherein the second occlusion element is shaped so as to allow fluid to flow past it more readily than the first occlusion element.

* * * * *